(12) United States Patent
Egusa

(10) Patent No.: US 9,463,204 B2
(45) Date of Patent: Oct. 11, 2016

(54) METHOD FOR INDUCING DIFFERENTIATION ENABLING TUMORIGENESIS OF IPS CELLS TO BE SUPPRESSED

(71) Applicant: Osaka University, Suita-shi, Osaka (JP)

(72) Inventor: Hiroshi Egusa, Suita (JP)

(73) Assignee: Osaka University, Suita-shi, Osaka (JP)

( * ) Notice: Subject to any disclaimer, the term of this patent is extended or adjusted under 35 U.S.C. 154(b) by 0 days.

(21) Appl. No.: 14/369,157

(22) PCT Filed: Dec. 27, 2012

(86) PCT No.: PCT/JP2012/083945
§ 371 (c)(1),
(2) Date: Jun. 26, 2014

(87) PCT Pub. No.: WO2013/100080
PCT Pub. Date: Jul. 4, 2013

(65) Prior Publication Data
US 2014/0356336 A1    Dec. 4, 2014

(30) Foreign Application Priority Data
Dec. 27, 2011 (JP) .................. 2011-286906

(51) Int. Cl.
| | |
|---|---|
| A61K 35/32 | (2015.01) |
| C07D 209/26 | (2006.01) |
| C07D 309/30 | (2006.01) |
| C12N 5/074 | (2010.01) |
| A61K 31/40 | (2006.01) |
| A61K 31/405 | (2006.01) |
| A61K 31/44 | (2006.01) |
| A61K 31/505 | (2006.01) |

(52) U.S. Cl.
CPC ............ *A61K 35/32* (2013.01); *A61K 31/40* (2013.01); *A61K 31/405* (2013.01); *A61K 31/44* (2013.01); *A61K 31/505* (2013.01); *C07D 209/26* (2013.01); *C07D 309/30* (2013.01); *C12N 5/0696* (2013.01); *C12N 2501/71* (2013.01); *C12N 2501/999* (2013.01)

(58) Field of Classification Search
None
See application file for complete search history.

(56) References Cited

U.S. PATENT DOCUMENTS

| | | |
|---|---|---|
| 2003/0220343 A1 | 11/2003 | Ohsawa et al. |
| 2004/0014712 A1 | 1/2004 | Ohsawa et al. |
| 2010/0010099 A1 | 1/2010 | Chiou et al. |
| 2010/0190250 A1 | 7/2010 | Hu |
| 2012/0237560 A1 | 9/2012 | Soo et al. |
| 2012/0244128 A1 | 9/2012 | Soo et al. |

FOREIGN PATENT DOCUMENTS

| | | |
|---|---|---|
| WO | WO 2006/024026 A2 | 3/2006 |
| WO | WO 2010/120785 A2 | 10/2010 |
| WO | WO 2011/022070 A2 | 2/2011 |

OTHER PUBLICATIONS

Majlesi, et al. (2003) "Cerivastatin and atorvastatin inhibit IL-3-dependent differentiation and IgE-mediated histamine release in human basophils and downmodulate expression of the basophil-activation antigen CD203c/E-NPP3", Journal of Leukocyte Biology, 73(1): 107-17.*
Brock, et al. (2011) "Reference Maps of Human ES and iPS Cell Variation Enable High-Throughput Characterization of Pluripotent Cell Lines", Cell, 144: 439-52.*
Shachaf, et al. (2007) "Inhibition of HMGcoA reductase by atorvastatin prevents are reverses MYC-induced lymphomagenesis", Blood, 110(7): 2674-84.*
Maeda, et al. (2004) "Induction of osteoblast differentiation indicies by statins in MC3T3-E1 cells", Journal of Cellular Biochemistry, 92(3): 458-71.*
Illich, et al. (2011) "Concise Review: Induced Pluripotent Stem Cells and Lineage Reprogramming: Prospects for Bone Regeneration", Stem Cells, 29: 555-63.*
Takahashi, et al. (2007) "Induction of Pluripotent Stem Cells from Adult Human Fibroblasts by Defined Factors", Cell, 131(11): 861-72.*
International Search Report for Japanese PCT Application PCT/JP2012/083945 mailed Mar. 26, 2013 (in 4 pages).
Kawamoto, A. et al. 2006 "Effect of hyaluronan on proliferation, migration and gel contraction in osteoblast-like cells", *Shika Igaku* 69: 182-183.
Kayashima, H. et al. 2012 "Efficient Osteogenic Induction of iPS Cells without Tumor Formation—Toward Autologous Cell-Derived Bone Graft Materials-" *Ann Jpn Prosthodont Soc* (p. 238).
Lee, S.K. et al., 2010 "Stabilization and translocation of p53 to mitochondria is linked to Bax translocation to mitochondoria in simvastation-induced apoptosis" *Biochem. Biophys. Res. Comm.* 391: 1592-1597.
Miura, K. et al., 2009 "Variation in the safety of induced pluripotent stem cell lines" *Nature Biotechnology* 27(8): 743-745.
Ochiai, T. et al., 2008 "Cholesterol-independent, MAPK/ERK signal-mediated simvastatin potentiation of nerve growth factor-induced neurite outgrowth in PC-12 cells" *Parmaceutical Bulletin of Fukuoka University* 8: 146-159.
Lee A.S. et al., 2013 "Tumorigenicity as a clinical hurdle for pluripotent stem cell therapies" *Nature Medicine* 19: 998-1004.
European Search Report for European Application No. 12863354.2 dated May 7, 2015 in 7 pages.

* cited by examiner

Primary Examiner — Robert M Kelly
(74) Attorney, Agent, or Firm — Knobbe, Martens Olson & Bear, LLP

(57) ABSTRACT

The object of the invention is to provide a technique of suppressing tumorigenesis in IPS cells and inducing differentiation into target differentiated cells. In use of a statin and a differentiation inducer, iPS cells are differentiated into target differentiated cells, whereby iPS cells can be differentiated into differentiated cells in which tumorigenesis is suppressed.

9 Claims, 13 Drawing Sheets

METHOD FOR INDUCING DIFFERENTIATION ENABLING TUMORIGENESIS OF IPS CELLS TO BE SUPPRESSED

TECHNICAL FIELD

The present invention relates to a technique for differentiating iPS cells into target differentiated cells while suppressing tumorigenesis in the iPS cells.

REFERENCE TO SEQUENCE LISTING

The present application is filed along with a Sequence Listing in electronic format. The Sequence Listing is provided as a file entitled 18298743_1.TXT, created Jun. 26, 2014, which is approximately 2.12 KB in size. The information in the electronic format of the Sequence Listing is incorporated herein by reference in its entirety.

BACKGROUND ART

Human iPS cells have been established (see for example Non-Patent Document 1 and Patent Document 1), and hold promise in the field of regenerative medicine. iPS cells, also called artificial pluripotent stem cells or induced pluripotent stem cells, are cells with acquired pluripotency, and these cells acquire pluripotency by the introduction of genes coding for various kinds of transcription factors, such as Oct family (Oct3/4), Sox family (Sox2, Sox1, Sox3, Sox15, Sox 17, etc.), Klf family (Klf4, Klf2, etc.), Myc family (c-Myc, N-Myc, L-Myc, etc.), Nanog and LIN28 transcription factors, that confer pluripotency on somatic cells (such as fibroblasts for example).

Cells that are known to be pluripotent include ES cells as well as iPS cells, but with ES cells there are problems of bioethics because the cells are obtained from pre-implantation stage embryos, hence there have been problems in using such cells in regenerative medicine. Such problems can be avoided with iPS cells because they can be established from skin and cells, which are relatively easy to obtain. Moreover, iPS cells also hold promise for advancing regenerative medicine because they can be obtained from the tissue of a patient requiring treatment, thus eliminating the risk of immune rejection.

Recently, attempts have been made in the fields of dentistry and orthopedic surgery to induce differentiation of iPS cells into osteoblasts, which can then be used to regenerate alveolar bone and cartilage. In the dental field for example, dental implant treatment and prosthodontic treatment are often difficult in cases of patients who have lost teeth, due to bone loss in the jaw. In such cases, implantation and the like can be accomplished if osteoblasts are transplanted to the area of bone loss in the jaw, and used to regenerate alveolar bone. Osteoblasts obtained by inducing differentiation of iPS cells established from somatic cells of the same patient do not pose a risk of immune rejection. Moreover, the inventors have confirmed that the efficiency of iPS cell establishment is extremely high using oral epithelial cells and oral fibroblasts (see for example Patent Document 2).

Because iPS cells are pluripotent, however, there have been serious problems with tumorigenesis after implantation. Methods that have been proposed for solving this problem include a method using iPS cell tumorigenesis markers to sort and remove tumorigenic cells (see for example Non-Patent Document 2), and a method using iPS cells that have been directed to the target tissue in vitro, in which the cells are cell sorted by FACS or the like, and target cells are selected and used in transplantation. However, drawbacks of these methods include the difficulty of securing adequate numbers of cells, and the risk of contamination.

Thus, iPS cells hold promise in the field of regenerative medicine, but because of such problems they have yet to be put into practical use. That is, the challenge for achieving clinical application of iPS cells is to find ways of suppressing tumorigenesis.

Meanwhile, HMG-CoA reductase inhibitors (statins) are in wide clinical use to treat high cholesterol by inhibiting cholesterol synthesis. In recent years, it has been confirmed that statins have diverse pharmacological effects on differentiation and proliferation of various cells. However, it was not known that tumorigenesis could be suppressed by culturing iPS cells in the presence of statins.

Non-Patent Document 1: Takahashi K. et al. (2007), "Induction of Pluripotent Stem Cells from Adult Human Fibroblasts by Defined Factors", Cell 131:861-872.

Non-Patent Document 2: Tang C et al., "An antibody against SSEA-5 glycan on human pluripotent stem cells enables removal of teratoma-forming cells", Nat. Biotechnol. 2011; 29(9):829-34.

Patent Document 1: WO 2007/069666
Patent Document 2: WO 2011/024550

DISCLOSURE OF THE INVENTION

It is an object of the present invention to provide a technique for differentiating iPS cells into target differentiated cells while suppressing tumorigenesis in the iPS cells.

The inventors discovered as a result of exhaustive research aimed at solving the aforementioned problems that tumorigenesis of iPS cells could be suppressed by culturing iPS cells in the presence of statins. The inventors also confirmed that differentiated cells in which tumorigenesis was suppressed could be obtained by using a statin and a differentiation inducer to induce differentiation of iPS cells into differentiated cells. The present invention was perfected as the result of exhaustive research based on such findings. That is, the present invention provides a method based on a mode as described below, a tumorigenesis suppressor, a medium, iPS cells in which tumorigenesis is suppressed, a tissue regeneration method and the like.

1. A method for inducing differentiation of iPS cells while suppressing tumorigenesis, this method including a step of differentiating iPS cells into target differentiated cells, using a statin and a differentiation inducer that causes differentiation of iPS cells into the target differentiated cells.

2. The differentiation inducing method according to 1 above, wherein the statin is a compound represented by General Formula (A) below:

General Formula (A):

in General Formula (A), the carboxyl group may form a ring structure with the hydroxyl group of the third position, and Ri represents any of the groups shown in General Formulae (1) to (6) below:

General Formula (1):

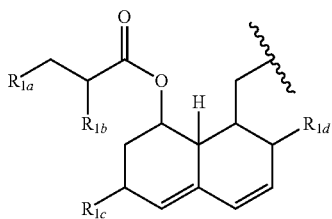

in General Formula (1), $R_{1a}$ and $R_{1b}$ may be the same or different, and are each hydrogen atoms or $C_{1-5}$ linear or branched alkyl groups; and $R_{1c}$ and $R_{1d}$ may be the same or different, and are each hydrogen atoms, hydroxyl groups or $C_{1-5}$ linear or branched alkyl groups;

General Formula (2):

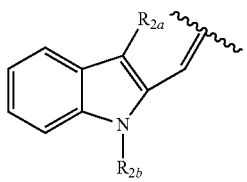

in General Formula (2), $R_{2a}$ is a halogen-substituted phenyl group, and $R_{2b}$ is a $C_{1-5}$ linear or branched alkyl group;

General Formula (3):

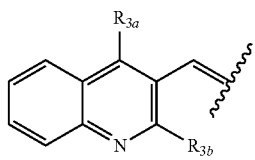

in General Formula (3), $R_{1a}$ is a halogen-substituted phenyl group, and $R_{3c}$ is a $C_{3-5}$ cycloalkyl group;

General Formula (4):

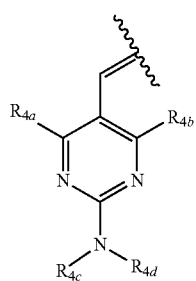

in General Formula (4), $R_{4a}$ is a halogen-substituted phenyl group, $R_{4b}$ and $R_{4c}$ may be the same or different, and are each $C_{1-5}$ linear or branched alkyl groups, and $R_{4d}$ is a $C_{1-4}$ alkylsulfonyl group;

General Formula (5):

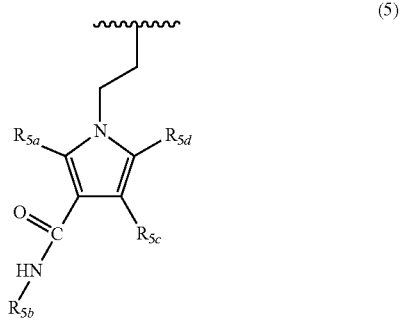

in General Formula (5), $R_{5a}$ is a $C_{1-5}$ linear or branched alkyl group, and $R_{5b}$, $R_{5c}$ and $R_{5d}$ may be the same or different, and are each phenyl groups or halogen-substituted phenyl groups;

General Formula (6):

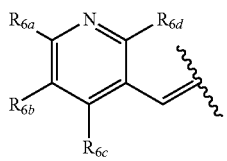

in General Formula (6), $R_{6a}$ and $R_{6d}$ may be the same or different, and are each $C_{1-5}$ linear or branched alkyl groups, $R_{6b}$ is a $C_{1-5}$ alkoxy group, and $R_{6c}$ is a halogen-substituted phenyl group.

3. The differentiation inducing method according to 1 above, wherein the statin is at least one selected from the group consisting of simvastatin, fluvastatin, lovastatin, atorvastatin, pitavastatin, pravastatin and rosuvastatin.

4. The differentiation inducing method according to 1 above, wherein the iPS cells are differentiated into the target differentiated cells by culturing the iPS cells in a medium containing the statin and the differentiation inducer.

5. The differentiation inducing method according to 1 above, wherein the iPS cells are differentiated into the target differentiated cells by first culturing the iPS cells in a medium containing the statin, and then culturing the same in a medium containing the differentiation inducer.

6. The differentiation inducing method according to 1 above, wherein the concentration of the statin is 0.01 to 10 μM.

7. The differentiation inducing method according to 1 above, wherein the iPS cells are derived from epithelial cells of the oral mucous membrane or fibroblasts of the oral mucous membrane.

8. The differentiation inducing method according to 1 above, wherein iPS cells are differentiated into osteoblasts, using a statin and a differentiation inducer that causes differentiation of iPS cells into osteoblasts.

9. A method of preparing a cell preparation containing differentiated cells in which tumorigenesis is suppressed, the method including: a step of differentiating iPS cells into target differentiated cells, using a statin and a differentiation inducer that causes differentiation of iPS cells into the target differentiated cells; and a step of preparing a cell preparation, using the differentiated cells obtained in the previous step.

10. The method of preparing a cell preparation according to 9 above, wherein the differentiated cells are osteoblasts.

11. A medium for obtaining differentiated cells, in which tumorigenesis is suppressed, from iPS cells, the medium containing a statin and a differentiation inducer that causes differentiation of iPS cells into target differentiated cells.

12. Use of a statin to manufacture a medium for obtaining differentiated cells, in which tumorigenesis is suppressed, from iPS cells.

13. A method for suppressing tumorigenesis when differentiating iPS cells into differentiated cells, the method including a step of differentiating the iPS cells into target differentiated cells, using a statin and a differentiated inducer that causes differentiation of the iPS cells into the target differentiated cells.

14. A method for suppressing tumorigenesis of iPS cells, the method including a step of culturing the iPS cells in the presence of a statin.

15. An iPS cell tumorigenesis suppressor, containing a statin as an active ingredient.

16. The tumorigenesis suppressor according to 15 above, which is used when differentiating iPS cells into osteoblasts.

17. Use of a statin to manufacture an iPS cell tumorigenesis suppressor.

18. iPS cells, in which tumorigenesis is suppressed, obtained by culturing iPS cells in the presence of a statin.

19. A statin used to suppress tumorigenesis of iPS cells.

20. An apoptosis inducer having a statin as an active ingredient and used to induce apoptosis of iPS cells having the property of non-differentiation, when inducing differentiation of iPS cells.

21. A bone regenerating agent, containing osteoblasts obtained by culturing iPS cells in the presence of a statin and a differentiation inducer that induces differentiation into osteoblasts.

22. A tissue regeneration method comprising:
(i) a step of differentiating iPS cells into target differentiated cells, using a statin and a differentiation inducer that causes differentiation of the iPS cells into target differentiated cells;
(ii) a step of using the differentiated cells obtained in the previous step to prepare a cell preparation; and
(iii) a step of administering the cell preparation obtained in the step (ii) to a patient in need of tissue regeneration.

The statins used in the invention are already widely used as cholesterol reducers, and their pharmacokinetics and effects on the human body have been analyzed in detail. One serious issue for achieving the use of iPS cells in regenerative medicine is how to prevent the iPS cells from causing tumorigenesis at the transplant site. With the present invention, it is possible to solve this problem of tumorigenesis. That is, differentiated cells in which tumorigenesis is dramatically suppressed after transplantation can be obtained by differentiating iPS cells using a statin and a differentiation inducer that induces differentiation into the target differentiated cells, and formation of teratomas in the living body (tumorigenesis) is not a concern when such cells are transplanted. Thus, the present invention can contribute greatly to achieving regenerative medicine using iPS cells.

Because tumorigenesis after transplantation is suppressed in osteoblasts obtained by inducing differentiation of iPS cells in the presence of a statin and an osteoblast differentiation inducer, it is possible to provide osteoblasts with high practical utility for regeneration of bone tissue. With such a method, moreover, because differentiation of iPS cells into osteoblasts is sufficiently directed, it is possible to efficiently obtain osteoblasts in which tumorigenesis is suppressed without going through complex procedures such as cell sorting to obtain uniformly differentiated cells.

The present invention also provides a method for inducing differentiation of iPS cells with a differentiation inducer in the presence of a statin and preparing a cell preparation containing the resulting differentiated cells, and tumorigenesis is suppressed in the cell preparation obtained by this method, which is thus extremely safe in the body. The present invention also provides a tissue regeneration method, comprising a step of administering such a cell preparation to a patient. In addition, the invention also provides a medium containing a statin and a differentiation inducer, used to obtain differentiated cells in which tumorigenesis is suppressed from iPS cells, as well as a method for suppressing tumorigenesis when differentiating iPS cells into differentiated cells, a method for suppressing tumorigenesis of iPS cells, an iPS cell tumorigenesis suppressor, and iPS cells in which tumorigenesis is suppressed and the like.

BRIEF DESCRIPTION OF THE DRAWINGS

FIG. 3A shows a histological image by H&E staining of a graft of mouse iPS cells that were subjected to differentiation induction for 30 days in osteoblast differentiation-inducing medium (containing no simvastatin), transplanted, and then extracted after 28 days; Various histologies typical of teratomas were recognized around the aggregate (*) of transplanted cells; FIG. 3B shows a histological image by H&E staining of a graft of mouse iPS cells that had been subjected to differentiation induction for 30 days in osteoblast differentiation-inducing medium containing simvastatin, transplanted, and then extracted after 28 days; and only formation of bone-like hard tissue and fibrous immature bone was observed around the aggregate (*) of transplanted cells.

BEST MODE FOR CARRYING OUT THE INVENTION

Figure 1:
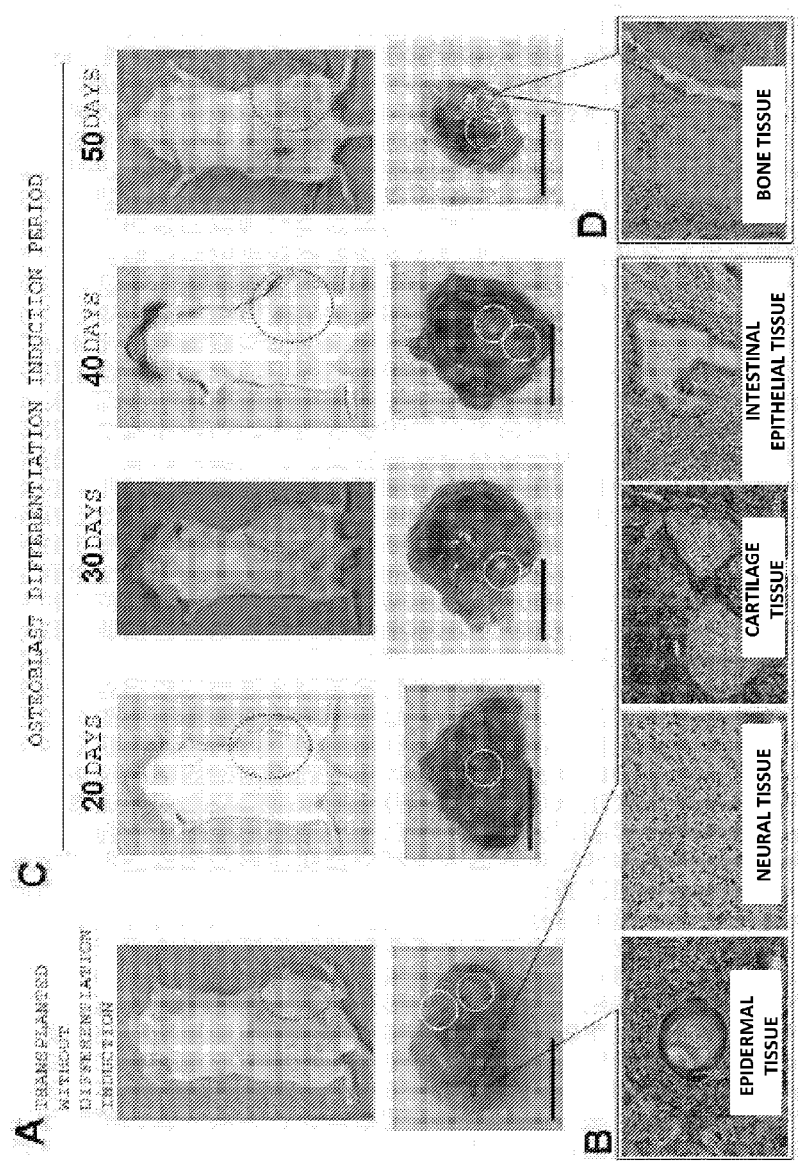
FIG. 1A shows a tumor (broken circle) formed 28 days after transplantation by mouse iPS cells transplanted without osteoblast differentiation induction; Obvious tumor formation was confirmed around the extracted graft (white circle) (Bar: 1 cm)
FIG. 1B shows the results of hematoxylin and eosin (H&E) staining of tissue sections from the tumor of FIG. 1A; The tumor was confirmed to be a teratoma containing various tissues derived from all three germ layers.
FIG. 1C shows tumors (broken circles) formed 28 days after transplantation of cells obtained by inducing differentiation of iPS cells for 20, 30, 40 and 50 days in osteoblast differentiation-inducing medium; Obvious tumor formation was confirmed around the extracted tissue sections (white circles) (Bar: 1 cm)
FIG. 1D shows osteoblast formation around a graft of cells obtained by inducing differentiation of iPS cells into osteoblasts for 50 days.

1. Method for Inducing Differentiation of iPS Cells

The present invention provides a method for inducing differentiation of iPS cells, in which iPS cells are differentiated into target differentiated cells while suppressing tumorigenesis by using a statin together with a differentiation inducer for inducing differentiation into the target differentiated cells. This method is explained in detail below.

[Statin]

"Statin" is a general term for compounds that reduce blood cholesterol values by inhibiting the action of HMG-CoA reductase, and which are used as treatment drugs for high cholesterol.

The statin used in the present invention is represented by the following general formula.

General Formula (a):

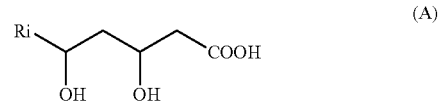

in which the carboxyl group may form a ring structure with the hydroxyl group of the third position.

Ri represents a group shown by any of General Formulae (1) to (6) below.

General Formula (1):

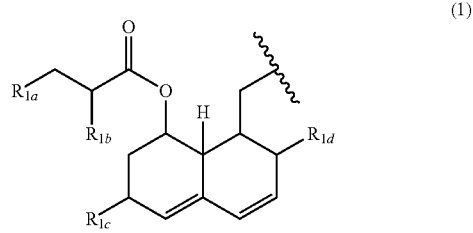

in which $R_{1a}$ and $R_{1b}$ may be the same or different, and are each hydrogen atoms or $C_{1-5}$ linear or branched alkyl groups, and $R_{1c}$ and $R_{1d}$ may be the same or different, and are each hydrogen atoms, hydroxyl groups or $C_{1-5}$ linear or branched alkyl groups.

Examples of the $C_{1-5}$ linear or branched alkyl groups include methyl, ethyl, n-propyl, isopropyl, n-butyl, sec-butyl, tert-butyl and pentyl groups. A methyl group is preferred in General Formula (1).

In General Formula (1), $R_{1a}$ is preferably a hydrogen atom or methyl group, $R_{1b}$ is preferably a hydrogen atom, methyl group or isopropyl group, $R_{1c}$ is preferably a hydrogen atom, hydroxyl group or methyl group, and $R_{1d}$ is preferably a hydrogen atom or methyl group; examples of specific compounds include pravastatin, lovastatin, simvastatin and mevastatin.

General Formula (2):

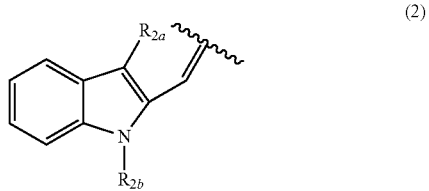

in which $R_{2a}$ is a halogen-substituted phenyl group, and $R_{2b}$ is a $C_{1-5}$ linear or branched alkyl group.

The halogen-substituted phenyl group represented by $R_{2a}$ is a phenyl group substituted with either the same or different halogen atoms. Examples of halogen atoms include fluorine, chlorine, bromine and the like, and fluorine is preferred. The number of halogen atom substitutions is one or more, and is preferably one. The position of the carbon substituted with the halogen atom may be any of positions 2 to 6, or preferably any of positions 2 to 5, or more preferably position 4. Preferred examples of halogen-substituted phenyls include 2-fluorophenyl and 4-fluorophenyl groups and the like, and a 4-fluorophenyl group is preferred.

The $C_{1-5}$ linear or branched alkyl group represented by $R_{2b}$ is as defined in General Formula (1) above, and is preferably an isopropyl group.

In General Formula (2), preferably $R_{2a}$ is a 4-fluorophenyl group and $R_{2b}$ is an isopropyl group. An example of such a specific compound is fluvastatin.

General Formula (3):

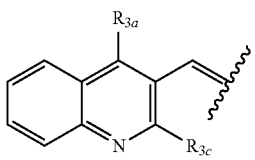

(3)

in which $R_{3a}$ is a halogen-substituted phenyl group, and $R_{1c}$ is a $C_{3-5}$ cycloalkyl group.

The halogen-substituted phenyl group represented by $R_{3a}$ is as defined in General Formula (2) above, and is preferably a 4-fluorophenyl group.

The $C_{3-5}$ cycloalkyl group represented by $R_{3b}$ may be a cyclopropyl group or cyclobutyl group, and is preferably a cyclopropyl group.

In General Formula (3), preferably $R_{3a}$ is a 4-fluorophenyl group, and $R_{3b}$ is a cyclopropyl group. An example of such a specific compound is pitavastatin.

General Formula (4):

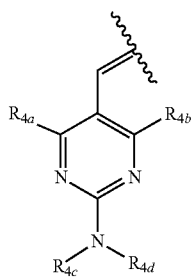

(4)

in which $R_{4a}$ is a halogen-substituted phenyl group, $R_{4b}$ and $R_{4c}$ are the same or different and are each $C_{1-5}$ linear or branched alkyl groups, and $R_{4d}$ is a $C_{1-4}$ alkylsulfonyl group.

The halogen-substituted phenyl group represented by $R_{4a}$ is as defined in General Formula (2) above, and is preferably a 4-fluorophenyl group.

A $C_{1-5}$ linear or branched alkyl group represented by $R_{4b}$ or $R_{4c}$ is as defined in General Formula (1) above, and is preferably a methyl group or isopropyl group.

Examples of the $C_{1-6}$ alkylsulfonyl group represented by $R_{4d}$ include methylsulfonyl, ethylsulfonyl, propylsulfonyl, isopropylsulfonyl, butylsulfonyl, isobutylsulfonyl, sec-butylsulfonyl and tert-butylsulfonyl groups and the like, and a methylsulfonyl group is preferred.

In General Formula (4), preferably $R_{4a}$ is a 4-fluorophenyl group, $R_{4b}$ is an isopropyl group, $R_{4c}$ is a methyl group and $R_{4d}$ is a methylsulfonyl group. An example of such a specific compound is rosuvastatin.

General Formula (5):

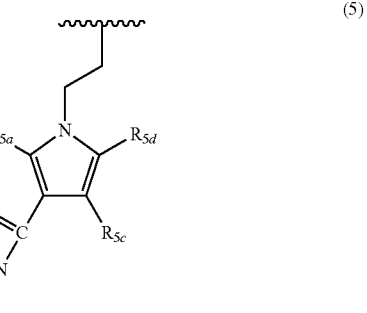

(5)

in which $R_{5a}$ is a $C_{1-5}$ linear or branched alkyl group, and $R_{5b}$, $R_{5c}$ and $R_{5d}$ are the same or different and are phenyl groups or halogen-substituted phenyl groups.

The $C_{1-5}$ linear or branched alkyl group represented by $R_{5a}$ is as defined in General Formula (1) above, and is preferably an isopropyl group.

When the phenyl groups or halogen-substituted phenyl group represented by $R_{5b}$, $R_{5c}$ and $R_{5d}$ are halogen-substituted phenyl groups, they are as defined in General Formula (2) above, and are preferably 4-fluorophenyl groups. In General Formula (5), $R_{5b}$ and $R_{5c}$ are preferably phenyl groups, and $R_{5d}$ is preferably a 4-fluorophenyl group.

In General Formula (5), preferably $R_{5a}$ is an isopropyl group, $R_{5b}$ and $R_{5c}$ are phenyl groups, and $R_{5d}$ is a 4-fluorophenyl group. An example of such a specific compound is atorvastatin.

General Formula (6):

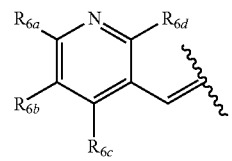

(6)

in which $R_{6a}$ and $R_{6d}$ are the same or different and are $C_{1-5}$ linear or branched alkyl groups, $R_{6b}$ is a $C_{1-5}$ alkoxy group, and $R_{6c}$ is a halogen-substituted phenyl group.

The $C_{1-5}$ linear or branched alkyl groups represented by $R_{6a}$ and $R_{6d}$ are as defined in General Formula (1) above, and are preferably isopropyl groups.

The $C_{1-5}$ alkoxy group represented by $R_{6b}$ may be methoxy, ethoxy, n-propoxy, n-butoxy, isopropoxy, isobutoxy, tert-butyoxy or n-pentyloxy group or the like, and is preferably an ethoxy group.

The halogen-substituted phenyl group represented by $R_{6c}$ is as defined in General Formula (2) above, and is preferably a 4-fluorophehyl group.

In General Formula (6), preferably $R_{6a}$ and $R_{6d}$ are both isopropyl groups, $R_{6b}$ is an ethoxy group, and $R_{6c}$ is a 4-fluorophenyl group. An example of such a specific compound is Cerivastatin.

These statins are classified into two types, lipophilic and hydrophilic, according to their physiochemical and pharmacokinetic characteristics. Specific examples of lipophilic statins include simvastatin, fluvastatin, atorvastatin, pitavastatin and the like. Specific examples of hydrophilic statins include lovastatin, pravastatin, rosuvastatin and the like. Either a hydrophilic statin or a lipophilic statin may be used in the present invention.

When a cell preparation prepared by the method of the invention is to be used in a living human body, it is desirable to use a statin such as simvastatin, fluvastatin, lovastatin, atorvastatin, pitavastatin, pravastatin, rosuvastatin and the like, which are marketed for treatment of hyperlipidemia and have been confirmed to be safe from a toxicity standpoint. Simvastatin, fluvastatin, lovastatin, pravastatin and mevastatin are preferred, and simvastatin, fluvastatin and lovastatin are more preferred. Of these, simvastatin is an example of an especially desirable statin.

The compounds represented by the general formulae above may be used in the form of pharmacologically acceptable salts, and may also be used in the form of hydrates. Derivatives of the compounds represented by the general formulae above may also be used.

There are no particular limits on the "pharmacologically acceptable salts", which may be selected appropriately as long as they do not detract from the effects of the invention, and examples include alkali metal salts, alkali earth metal salts and ammonium salts of sodium, potassium, lithium, calcium, magnesium, barium, ammonium and the like. These salts may also include acid addition salts produced by reactions between the compounds represented by the general formulae above and suitable organic acids or inorganic acids. Examples of acid addition salts include hydrochloride salts, sulfate salts, acetate salts, oxalate salts, borate salts, lactate salts, phosphate salts, citrate salts, maleate salts, fumarate salts, succinate salts, tartrate salts, sulfonate salts, glycolate salts, ascorbate salts, benzenesulfonate salts and the like. These salts may be prepared by methods known in the field. Of these salts, alkali metal salts and alkali earth metal salts are desirable examples, and sodium salts and calcium salts are especially desirable.

"Derivatives" here include those in which the position of a substituent has been changed, those in which one molecule has been replaced by another molecule, those in which a specific substituent has been added, and those in which a specific substituent has been removed or the like while maintaining the basic framework represented by the general formula. There are no particular limits on what derivatives can be used in the invention as long as they act on iPS cells, but lactones and esters are desirable for example.

One of these statins may be used alone in the present invention, or two or more may be used in combination.

[Differentiation Inducer]

Differentiation inducers that induce differentiation of iPS cells into differentiated cells are well known, and a differentiation inducer may be selected appropriately according to the target differentiated cells in the present invention.

For example, inducers of differentiation into osteoblasts include ascorbic acid, β-glycerophosphoric acid, dexamethasone, BMP-2, hydrocortisone hemisuccinate, retinoic acid and the like; inducers of differentiation into nerve cells include nerve growth factor (NGF), brain derived nerve growth factor (BDNF), retinoic acid and the like; inducers of differentiation into liver cells include hexachlorophene, quercetin, ionomycin and the like; inducers of differentiation into fat cells include allyl isothiocyanate, cinnamaldehyde, icilin and the like; inducers of differentiation into myocardial cells include BMP-4, BMP-5, FGF-10, cyclosporine A, ascorbic acid and the like; inducers of differentiation into epithelial cells include apoptosis signal-regulating kinase 1 (ASK1) and the like; and inducers of differentiation into retinal pigment epithelial cells include retinoic acid, taurine and the like. For purposes of inducing differentiation into osteoblasts, the ascorbic acid may be ascorbic acid-2-phosphate or a salt thereof. Moreover, hydrocortisone hemisuccinate may be used in place of dexamethasone for purposes of inducing differentiation into osteoblasts. Each of the differentiation inducers used for differentiation into these different kinds of cells may be used individually, or a combination of two or more may be used.

Desirable examples of differentiation inducers for use in the present invention include inducers of differentiation into osteoblasts, particularly such osteoblast differentiation inducers as ascorbic acid, β-glycerophosphoric acid and dexamethasone.

[iPS Cells]

"iPS cells", also called artificial pluripotent stem cells or induced pluripotent stem cells, are cells with acquired pluripotency, which have acquired pluripotency equivalent to that of ES cells by the introduction of various kinds of transcription factors (hereunder called "reprogramming factors") that confer pluripotency on somatic cells (such as fibroblasts for example).

Reprogramming Factors

Various kinds of reprogramming factors are used in establishing iPS cells, and many combinations are known. Any conventionally known reprogramming factor capable of establishing iPS cells may be used in the present invention, without any particular limits. Moreover, reprogramming factors and combinations of reprogramming factors that are discovered in the future may also be adopted.

Specific examples of reprogramming factors include Oct3/4, Oct1A, Oct6, Klf4, Klf1, Klf2, Klf5, c-Myc, N-Myc, L-Myc, Lin28b, Sox1, Sox2, Sox3, Sox7, Sox15, Sox17, Sox18, Fbx15, Nanog, Eras, ECAT15-2, TclI, β-catenin, TERT, SV40 Large T antigen (SV40LT), HPV16 E6, HPV16 E7, Bmil, Lin28, Lin28b, Esrrb and the like. One or more of these may be selected and used.

Known conventional combinations of reprogramming factors may be selected and used, and examples include (1) Oct3/4, Klf4, c-Myc; (2) Oct3/4, Klf4, c-Myc, Sox2; (3) Oct3/4, Klf4, c-Myc, Sox2, Fbx15, Nanog, Eras, ECAT15-2, TClI, β-catenin; (4) Oct3/4, Klf4, c-Myc, Sox2, TERT, SV40LT; (5) Oct3/4, Klf4, c-Myc, Sox2, TERT, HPV16 E6; (6) Oct3/4, Klf4, c-Myc, Sox2, TERT, HPV16 E7; (7) Oct3/4, Klf4, c-Myc, Sox2, TERT, HPV6 E6, HPV16 E7; (8) Oct3/4, Klf4, c-Myc, Sox2, TERT, Bmil; (9) Oct3/4, Klf4, Sox2; (10) Oct3/4, Sox2, Nanog, Lin28; (11) Oct3/4, Sox2, Nanog, Lin28, hTERT, SV40LT; (12) Oct3/4, Klf4, c-Myc, Sox2, Nanog, Lin28; (13) Oct 3/4, Klf4, c-Myc, Sox2, SV40LT; (14) Oct3/4, Klf4; (15) Oct3/4, c-Myc; (16) Oct3/4, Sox2; (17) Oct3/4, Sox2, Nanog; (18) Oct3/4, Sox2, Lin28; (19) Oct3/4, Sox2, c-Myc, Esrrb; (20) Oct3/4, Sox2, Esrrb; (21) Oct3/4, Klf4, L-Myc; (22) Oct3/4, Nanog; (23) Oct3/4, Klf4, c-Myc, Sox2, Nanog, Lin28, SV40LT; (24) Sox2, Klf4, L-Myc, Lin28 and the like. In these combinations of reprogramming factors, Sox2 may be replaced by Sox1, Sox3, Sox15, Sox17 or Sox 18, Klf4 may be replaced by Klf1, Klf2 or Klf5, c-Myc may be replaced by N-Myc or L-Myc, and Esrrb may be replaced by Esrrg. Of these combinations of reprogramming factors, combinations (2), (9) and (24) above are preferred examples.

Somatic cells may be reprogrammed by introducing these reprogramming factors in the form of proteins, mRNA or genes coding for the reprogramming factors. cDNA sequence data for the genes coding for each reprogramming factor can be obtained from a known database such as NCBI, and cDNA of the desired sequence can be isolated by conventionally known methods.

In addition to wild genes and wild gene products, these reprogramming factors may also be mutant gene products comprising multiple (such as 1 to 10, or preferably 1 to 6, or more preferably 1 to 4, or still more preferably 1 to 3, or especially 1 or 2) amino acids substituted, deleted, and/or inserted in the amino acid sequences of these gene products, and having functions equivalent to those of the wild gene products, or may be mutant genes coding for these mutant gene products. Examples include T58A mutant c-Myc, S33Y mutant β-catenin and other mutant gene products, and mutant genes coding for these.

Somatic Cells

Somatic cells that can be used in the present invention as starting materials for iPS cell preparations may be any mammalian (such as mouse or human) cells other than reproductive cells. Such somatic cells for iPS cell preparations can be obtained for example from any tissue such as skin, mucous membrane, muscle, nerves or the like. The degree of differentiation of the cells obtained from these tissues is also not particularly limited, and undifferentiated precursor cells including somatic stem cells may also be used. Examples of undifferentiated precursor cells include neural stem cells, hematopoietic stem cells, and mesenchymal stem cells (mesenchymal stem cells derived from bone marrow, fat, dental pulp, periodontal membrane, etc.).

These cells may be from any tissue or organ, but because the efficiency of iPS cell establishment is dramatically improved by using cells from the oral mucous membrane, fibroblasts of the oral mucous membrane, epithelial cells of the oral mucous membrane and the like are desirable, gingival fibroblasts and gingival epithelial cells are specifically desirable, and gingival fibroblasts are especially desirable. Not only are cells from the oral mucous membrane capable of establishing iPS cells with high efficiency, but they do not detract from the establishing efficiency of iPS cells after subculture, and are convenient and extremely practical for clinical use.

When the resulting iPS cells are to be used for regenerative medicine in humans, it is especially desirable to collect the somatic cells from the same patient or from another person with the same HLA type, so as not to cause rejection reactions.

Introduction of Reprogramming Factor

Either a gene (nucleic acid molecule) coding for the reprogramming factor or a gene product (protein) may be used to introduce a reprogramming factor into somatic cells, but a gene is desirable from the standpoint of improving the efficiency of iPS cell establishment. The reprogramming factor may be introduced by a known method commonly used for transfection into cells.

When using a gene coding for a reprogramming factor, introduction into cells can be accomplished by means of an expression vector containing the gene coding for the reprogramming factor. For example, using a virus vector as the expression vector, a plasmid containing the gene coding for the reprogramming factor is introduced into suitable packaging cells (such as Plat-E cells) or a complementary cell line (such as 293 cells), the virus vector produced in the culture supernatant is collected, and cells are infected with the vector by a method suited to that particular virus vector. An adenovirus, retrovirus or the like can be used as the virus vector.

When a plasmid vector, episomal vector or other non-viral vector is used as the expression vector, on the other hand, the vector may be introduced into cells by the lipofection method, liposome method, electroporation method, calcium phosphate co-precipitation method, DEAE dextran method, microinjection method, gene gun method or the like.

In the case of a gene product (protein) of the reprogramming factor, introduction into somatic cells can be accomplished by known conventional methods, such as methods using protein introduction reagents, methods using proteins fused with protein transduction domains (PTDs), microinjection methods and the like. A method in which the reprogramming factor (protein) is introduced together with polyarginine or CPPs may also be used.

To improve the efficiency of iPS cell establishment, a histone deacetylase (HDAC) inhibitor such as valproic acid (VPA), trichostatin A, sodium butyrate or suberoylanilide hydroxamic acid; a DNA methyltransferase inhibitor such as 5'-azacytidine; a G9a histone methyltransferase inhibitor such as BIX-01294, or another low-molecular-weight compound may be used in addition to the reprogramming factor.

Culture Methods

Prior to reprogramming, the somatic cells used as the starting material may be pre-cultured in known medium suited to the type of cells. Examples of such media include, but are not limited to, minimum essential medium (MEM) containing about 5% to 20% fetal bovine serum, Dulbecco's modified Eagle medium (DMEM), RPMI1640 medium, 199 medium, F12 medium and the like.

After contact with the reprogramming factor (and a low-molecular-weight compound for improving the efficiency of iPS cell establishment), the cells may be cultured under suitable conditions for ES cell culture. For example, in the case of mouse cells they may be cultured after addition of leukemia inhibitory factor (LIF) as a differentiation-inhibiting factor to one of the mediums for pre-culture given as examples above. In the case of human cells, basic fibroblast growth factor (bFGF), stem cell factor (SCF) or the like is preferably added instead of LIF. Mouse embryonic fibroblasts (MEF) that have been treated with radiation or an antibiotic to arrest cell division are normally included as feeder cells when culturing reprogrammed cells, but these may also be cultured in a feeder-free environment.

Selection of established iPS cells may be accomplished by a known conventional method, such as a method which uses recombinant somatic cells targeting a drug resistance gene and/or reporter gene at the locus of a gene (for example, Fbx15, Nanog, Oct3/4 or the like, preferably Nanog or Oct3/4) having specific high expression in pluripotent cells to select colonies positive for drug resistance and/or reporter activity; and a method of selection by visual observation of morphology (see for example Takahashi et al., Cell, 131, 861-872 (2007)).

Confirming Non-Differentiation and Pluripotency

It is desirable to verify that the iPS cells obtained by these methods have the property of non-differentiation, and are pluripotent. In this Description, saying that iPS cells "have the property of non-differentiation" or "are pluripotent" means that the iPS cells have not differentiated into any specific cells, and such iPS cells pose the risk of tumorigenesis (teratoma formation) in the living body. As described in the context of methods for confirming the pluripotency of iPS cells below, tumorigenesis means the formation of a teratoma or other tumor when the iPS cells are transplanted into a model animal (SCID mouse or the like). When a teratoma forms, formation of cell aggregates (tissues) derived from the three germ layers is confirmed in the teratoma.

There are no particular limits on the method of confirming that the resulting iPS cells are undifferentiated, and one example is a method of detecting the mRNA of a conventionally known non-differentiation marker (for example, endogenous alkali phosphatase, Oct3/4, Sox2, Nanog, Eras, Esg1 or the like) used as an indicator. These markers may also be confirmed by immunochemical means (such as immune staining, Western blotting, ELISA or the like).

The method of confirming the pluripotency of the resulting iPS cells is also not particularly limited, and one example is a method of transplanting iPS cells into an immunodeficient model animal (SCID mouse or the like), and confirming the presence or absence of teratomas. If formation of cell aggregates (tissues) derived from the three germ layers is confirmed in the teratomas, the iPS cells are judged to have pluripotency.

When inducing iPS cells to differentiate into target differentiated cells that are then transplanted, iPS cell aggregates may be formed in advance of differentiation induction, and then induced to differentiate into the target cells and transplanted. One method of forming iPS cell aggregates is to prepare a gel of the temperature-responsive polymer poly N-isopropylacrylamide (pNIPAAm) with indentations 0.5 to 2 mm in diameter in accordance with the methods described in Sasaki et al.: Tissue Eng. Part A, 16(8): 2497-504, 2010 for example, and then seed iPS cells in the indentations to obtain iPS cell aggregates of the desired size. Because the cells can be transplanted as cell aggregates of the desired size without relying on a scaffold (cell culture substrate), differentiation induction using iPS cell aggregates is convenient and likely to result in efficient regeneration of target tissue.

[Differentiation of iPS Cells into Target Differentiated Cells]

Differentiated cells with suppressed tumorigenesis at the transplant site are obtained by using a statin and a differentiation inducer to differentiate iPS cells into target differentiated cells.

In the differentiation induction method of the present invention, differentiated cells in which tumorigenesis is suppressed can be obtained from iPS cells by bringing a statin and a differentiation inducer into contact with the iPS cells during culture, either sequentially or simultaneously. Specific methods include (1) a method of culturing iPS cells in a medium containing a statin and a differentiation inducer to differentiate them into the target differentiated cells, and (2) a method of culturing iPS cells in a medium containing a statin, and then culturing the resulting iPS cells in a medium containing a differentiation inducer to differentiate them into the target differentiated cells. Method (1) above is preferred from the standpoint of more efficiently obtaining differentiated cells in which tumorigenesis is surpressed.

The statin concentration when the iPS cells are brought into the contact with the statin (that is, the statin concentration in the medium) is not particularly limited as long as it is sufficient to suppress tumorigenesis, but is normally $10^{-2}$ to $10^2$ μM, or preferably 0.01 to 10 μM, or more preferably 0.1 to 10 μM, or still more preferably 0.5 to 10 μM, or yet more preferably 1 to 10 μM, or ideally 1 to 5 μM. For example, when the goal is to induce differentiation of iPS cells into osteoblasts, efficient differentiation into osteoblasts can be induced and tumorigenesis can be more effectively suppressed when transplanting the resulting osteoblasts if the statin is used within the aforementioned concentration range.

The concentration of the differentiation inducer when the iPS cells are brought into contact with the differentiation inducer (that is, the concentration of the differentiation inducer in the medium) can be set appropriately according to the type of differentiation inducer, the type of target differentiated cells and the like. For example, the concentration is normally $10^3$ to $10^6$ μM or preferably $10^{-2}$ to $10^5$ μM or more preferably $10^{-2}$ to $10^4$ μM when using an inducer of differentiation into osteoblasts. More specifically, when using a combination of ascorbic acid, β-glycerophosphoric acid and dexamethasone as inducers of differentiation into osteoblasts, the concentrations may be 1 to $10^3$ μM of ascorbic acid, $10^3$ to $10^6$ μM of β-glycerophosphoric acid and $10^{-3}$ to 1 μM of dexamethasone.

To differentiate iPS cells by bringing them into simultaneous contact with a statin and a differentiation inducer, the iPS cells can be cultured using a medium containing both the statin and a differentiation inducer in the aforementioned concentrations. To differentiate iPS cells by bringing them into sequential contact with a statin and a differentiation inducer, the iPS cells can first be cultured using a medium containing a statin in the aforementioned concentration, and then cultured after substituting for the medium a medium containing a differentiation inducer in the aforementioned concentration.

The concentration of the iPS cells when they are brought into sequential or simultaneous contact with a statin and a differentiation inducer during culture is not particularly limited, but is normally $1\times10^5$ to $1\times10^7$ cells/mL, or preferably $1\times10^6$ to $5\times10^6$ cells/mL, or more preferably $4\times10^6$ cells/mL The medium to which the statin and differentiation inducer are added individually or together is not particularly limited as long as it is one in which iPS cells can grow, and one example is minimum essential medium Eagle, alpha modification (α-MEM medium) containing 10% fetal bovine serum, 100 units/ml penicillin, 100 μg/ml streptomycin and 250 ng/ml amphotericin β.

The culture conditions for differentiating the iPS cells into the target differentiated cells are set appropriately according to the type of target differentiated cells and the like. For example, when culturing iPS cells in simultaneous contact with a statin and a differentiation inducer, the iPS cells can be cultured for about 1 to 50 days or preferably about 10 to 30 days in a medium containing both the statin and the differentiation inducer. Alternatively, when culturing iPS cells in contact with a statin and a differentiation inducer one after the other, the iPS cells can be cultured for about 1 to 20 days or preferably about 3 to 10 days in a medium containing the statin, and then further cultured for about 1 to 50 days or preferably about 10 to 30 days in a medium containing the differentiation inducer.

In particular, when inducing differentiation of iPS cells into osteoblasts, the iPS cells can be cultured for about 10 to 50 days or preferably for about 15 to 50 days or more preferably for about 15 to 40 days or still more preferably for about 20 to 30 days in medium containing an osteoblast inducer and a statin.

When culturing iPS cells in either sequential or simultaneous contact with a statin and a differentiation inducer, the dish can be moved back and forth with a see-saw bioreactor or the like to prevent the iPS cells from adhering to the dish.

Differentiated cells in which tumorigenesis is suppressed at the transplantation site are thus obtained by using a statin and a differentiation inducer to cause differentiation of iPS cells into the target differentiated cells.

It is possible to verify that the target differentiated cells have been obtained based on cell morphology and surface markers for each kind of differentiated cell. For example, when the target differentiated cells are osteoblasts, they can be verified based on whether they are positive for alkali phosphatase (ALP) activity, whether calcification of the extracellular matrix is found by Von Kossa staining or alizarin red staining, or whether an osteoblast-specific gene (collagen 1, osteocalcin, BSP, osterix, etc.) is expressed in RT-PCR analysis or the like. After transplantation of the osteoblasts, moreover, tissue at the transplantation site can be collected by biopsy, and formation of calcified bone tissue can be verified to confirm bone regeneration by osteoblasts. Formation of bone tissue can be confirmed by a known conventional method such as Von Kossa staining, hematoxylin and eosin (H&E) staining or the like.

There are no particular limits on the differentiated cells to which the differentiation induction method of the invention is applied, and examples include osteoblasts, nerve cells, liver cells, smooth muscle cells, fat cells, myocardial cells, epithelial cells, retinal pigment epithelial cells, dendritic cells and other immune cells and the like. The differentiation induction method of the present invention is particularly suited to differentiation into osteoblasts.

[Uses of Resulting Differentiated Cells]

Differentiated cells obtained by the differentiation induction method of the invention can be applied to various kinds of regenerative medicine according to the type of differentiated cells. Differentiated cells obtained by the differentiation induction method of the invention are effective in practical use in clinical fields because they allow tumorigenesis to be suppressed after transplantation.

For example, when the differentiated cells are osteoblasts they can be used therapeutically in plastic surgery, dentistry and other fields where bone regeneration is required. Bone regeneration includes regeneration of cartilage, alveolar bone, femoral bone and the like. In the dental field, patients who have lost teeth experience bone loss in the jaw, making dental implant therapy and denture therapy difficult, but alveolar bone can be reconstructed by transplanting osteoblasts obtained by the differentiation induction method of the invention to the bone loss site, allowing implantation and the like. The method of transplanting the resulting osteoblasts may be a conventionally known method, and may be selected appropriately according to the shape and condition of the transplantation site. Although direct transplantation of osteoblasts or colonies thereof to the target transplantation site is possible, one method for improving the graft survival rate of osteoblasts at a transplantation site is to mix osteoblasts obtained by the differentiation induction method of the invention with fibrinogen for example, after which thrombin is added to form a gel which is then transplanted to a site requiring bone regeneration. Another method of transplanting osteoblasts is to mix the osteoblasts with a bone supplement composed of hydroxyapatite, β-tricalcium phosphate (β-TCP) or the like before transplantation.

2. Method of Preparing Cell Preparation Containing Differentiated Cells in which Tumorigenesis is Suppressed The present invention also provides a method of preparing a cell preparation containing differentiated cells in which tumorigenesis is suppressed, comprising a step of using a statin and a differentiation inducer to cause differentiation of iPS cells into target differentiated cells, and a step of using the differentiated cells obtained in the previous step to prepare a cell preparation.

In this preparation method, the step of causing the iPS cells to differentiate into the target differentiated cells is as described under "1. Method for inducing differentiation of iPS cells" above. In this preparation method, the step of preparing the cell preparation is accomplished by collecting target differentiated cells that have been differentiated from iPS cells, and preparing them as a cell preparation. The method of collecting the differentiated cells is not particularly limited, and a conventionally known method may be selected appropriately, such as a method using an enzyme such as trypsin or a method using centrifugation or the like.

A cell preparation prepared by the method of the invention may consist solely of differentiated cells in which tumorigenesis is suppressed, but may also consist of the differentiated cells suspended in culture medium, isotonic solution, phosphate buffered saline (PBS) or the like with proteins such as albumin and other additives added thereto at will as long as this does not detract from the tissue regenerating ability or self-replicating ability of the cells. The differentiated cells prepared in this way may also be placed in a vial or other container for use as a cell preparation. Uses of the cell preparation prepared by the method of the invention are as described under "1. Method for inducing differentiation of iPS cells" above.

A cell preparation containing differentiated cells in which tumorigenesis is suppressed is obtained by the method of preparing a cell preparation of the invention. A cell preparation obtained in this way can be applied to various kinds of regenerative medicine according to the kind of differentiated cells. In one mode of the method of preparing a cell preparation of the invention, iPS cells are differentiated into osteoblasts by culturing them in the presence of a statin and a differentiation inducer that induces differentiation into osteoblasts, and then prepared as a cell preparation. A cell preparation obtained in this way may be used as a bone regenerating agent.

3. Method for Suppressing Tumorigenesis when Differentiating iPS Cells into Differentiated Cells The present invention provides a method for suppressing tumorigenesis when differentiating iPS cells into differentiated cells, comprising a step of using a statin and the aforementioned differentiation inducer to differentiate iPS cells into the target differentiated cells. The iPS cells, statin, differentiation inducer, and conditions for differentiating the iPS cells into the target differentiated cells and the like in this tumorigenesis suppression method are as described under "1. Method for inducing differentiation of iPS cells" above.

4. Method for Suppressing Tumorigenesis of iPS Cells

The present invention also provides a method for suppressing tumorigenesis of iPS cells, comprising a step of culturing the iPS cells in the presence of a statin. With this tumorigenesis suppression method, it is possible to confer a tumorigenesis suppressing effect on the iPS cells themselves. This tumorigenesis suppression method can be implemented by culturing the iPS cells in a culture containing a statin. The iPS cells, statin, and culture conditions in the medium containing the statin and the like in this tumorigenesis suppression method are as described under "1. Method for inducing differentiation of iPS cells" above.

Medium Used to Obtain Differentiated Cells in which Tumorigenesis is Suppressed from iPS Cells.

The present invention provides a medium containing a statin and the aforementioned differentiation inducer, used to obtain differentiated cells in which tumorigenesis suppressed from iPS cells. This medium is used favorably to obtain differentiated cells in which tumorigenesis is suppressed from iPS cells. The present invention also provides the use of a statin to manufacture a medium for obtaining differentiated cells in which tumorigenesis is suppressed from iPS cells. The type of the medium and the statin and differentiation inducer contained in the medium and the like are as described under "1. Method for inducing differentiation of iPS cells" above.

6. iPS Cell Tumorigenesis Suppressor

The invention provides an iPS tumorigenesis suppressor containing a statin as an active ingredient. iPS cells in which tumorigenesis is suppressed can be obtained by adding this tumorigenesis suppressor to medium when culturing iPS cells.

Moreover, differentiated cells in which tumorigenesis is suppressed after transplantation can be obtained by inducing differentiation of iPS cells into desired cells in the presence of both a predetermined differentiation inducer and the tumorigenesis suppressor. The methods for using this tumorigenesis suppressor and the like are similar to the methods of use and the like for the statin in "1. Method for inducing differentiation of iPS cells" above. The present invention also provides the use of a statin to manufacture an iPS cell tumorigenesis suppressor. The statin and the statin concentration and the like in this case are as described in "1. Method for inducing differentiation of iPS cells" above.

7. iPS Cells in which Tumorigenesis is Suppressed

The invention also provides iPS cells in which tumorigenesis is suppressed, obtained by culturing iPS cells in the presence of a statin. The culture conditions and the like for obtaining the iPS cells in which tumorigenesis is suppressed are as described in "1. Method for inducing differentiation of iPS cells" above.

8. Tissue Regeneration Method

The invention also provides a tissue regeneration method including:

(i) a step of differentiating iPS cells into target differentiated cells using a statin and a differentiation inducer that causes differentiation of the iPS cells into the target differentiated cells;

(ii) a step of using the differentiated cells obtained in the previous step to prepare a cell preparation; and (iii) a step of administering a cell preparation obtained in step (ii) above to a patient in need of tissue regeneration.

The iPS cells, statin, statin concentration, culture conditions and the like used in the tissue regeneration method of the invention are as described in "1. Method for inducing differentiation of iPS cells" above. In step (iii), a therapeutically effective dose of the cell preparation is administered to a patient in need of tissue regeneration. The form of administration is not particularly limited, and a known conventional method may be selected appropriately according to the type, location and size of the tissue to be regenerated and the age of the patient and the like. Examples include a method of transplanting an aggregate of differentiated cells to a site for regeneration, a method of injecting a cell suspension of differentiated cells into a site for regeneration, and a method of mixing the cells with a biological material as a carrier before injecting them into a site for regeneration.

9. Other

In the present invention, a statin is used to suppress tumorigenesis of iPS cells. That is, the present invention provides the use of a statin to suppress tumorigenesis of iPS cells. When using the statin, the iPS cells, statin, statin concentration and the like are as described in "1. Method for inducing differentiation of iPS cells" above.

Without trying to give a narrow interpretation of the present invention, it was hypothesized that statins induce apoptosis selectively in undifferentiated cells when inducing differentiation of iPS cells, and therefore the present invention provides an apoptosis inducer having a statin as an active ingredient, used to induce apoptosis in undifferentiated cells when inducing differentiation of iPS cells. The statin, statin concentration and the like in the apoptosis inducer are as described in "1. Method for inducing differentiation of iPS cells" above.

EXAMPLES

The present invention is explained in detail below with examples, but the invention is not limited to these examples.

Test Example 1

Preparation of Mouse iPS Cells and Differentiation into Osteoblasts (1) Preparation of Mouse iPS Cells Palatine mucosal tissue pieces (0.5 cm square) collected from 10-week-old male C57BL/6J mice were affixed to tissue culture plates that had been treated with an 0.1% gelatin coat, MF-start medium (Toyobo) was added, and the plates were left standing at 37° C. in the presence of 5% $CO_2$. Once adequate migration and proliferation of fibroblasts from the tissue pieces had been confirmed visually, a first subculture was performed, the medium was replaced with FP medium (sodium pyruvate-free Dulbecco's modified Eagle medium (Nacalai Tesque) containing 10% fetal bovine serum (Sigma), 50 units/ml penicillin and 50 µg/ml streptomycin (Invitrogen)), and culture was continued for 7 to 14 days.

These fibroblasts were used to establish an iPS cell line in accordance with the report of Egusa et al. (PLoS ONE, 5(9): e12743, 2010). Cell reprogramming was induced using a retrovirus vector (pMXs-IRES-puro: Addgene) incorporating the OCT3/4, Sox2 and Klf4 genes, together with a Platinum-E packaging cell system (Takahashi et al.: Nat. Protoc., 2(12): 3081-9, 2007). The established iPS cell line was maintained and cultured through 18 to 20 subcultures on SNLP76.7-4 feeder cells treated with mitomycin C, using ES medium (DMEM medium (Nacalai Tesque) containing 15% fetal bovine serum (Invitrogen), 2 mM L-glutamine (Invitrogen), $1 \times 10^4$ M nonessential amino acids (Invitrogen), $1 \times 10^4$ M 2-mercaptoethanol (Invitrogen), 50 U penicillin and 50 µg/ml streptomycin (Invitrogen)). Establishment of iPS cells was confirmed by the methods described in Egusa et al.: PLoS ONE, 5(9): e12743, 2010).

(2) Preparation of Mouse iPS Cell Aggregates iPS cell aggregates were prepared using a cell container made of a gel of the temperature-responsive polymer poly N-isopropyl acrylamide (pNIPAAm) (Sasaki et al.: Tissue Eng. Part A, 16(8): 2497-504, 2010). To prepare the container, a mold having surface protrusions 1.5 mm in diameter was prepared using three-dimensional modeling software (Free Form, Sensable, MA) with a three-dimensional printing system (Eden, Objet, Israel).

Next, the polymerization initiators ammonium persulfate (APS) (final concentration 1.6 mg/ml: Nacalai Tesque) and N,N,N,N-tetramethylethylene diamine (TEMED) (final concentration 1 µl/ml: Nacalai Tesque) were added to a mixed solution of the crosslinking agent polyethylene glycol dimethacrylate (Sigma) and a 7 mmol/L NIPAAm solution of hexane-purified N-isopropyl acrylamide (pNIPAAm) (Wako Pure Chemical) dissolved in ultrapure water, and poured into the prepared mold. This was left standing for 8 hours at 4° C. to obtain a cell container of pNIPAAm gel with surface indentations 1.5 mm in diameter. This gel was washed successively with ultrapure water, 70% ethanol and phosphate-buffered saline (PBS), and stored at 4° C. before being seeded with iPS cells.

Meanwhile, mouse iPS cells (after 18 to 20 subcultures) seeded at a concentration of about $0.5 \times 10^5$ to $0.5 \times 10^6$ cells/ml on 6-well tissue culture plates (0.1% gelatin coated) were collected by 0.25% trypsin treatment. This mouse iPS cell suspension liquid (about $1 \times 10^4$ to $1 \times 10^5$ cells/ml) was transferred to a 10 cm low-adherence culture dish containing ES medium, and suspension cultured for 2 more days. On the third day of culture, the iPS cells were collected by centrifugation (300 rpm, 2 minutes), and seeded ($1 \times 10^4$ to $1 \times 10^5$ cells/ml) on a low-adherence culture dish using ES medium containing 1 µM retinoic acid (all-transretinoic acid: Sigma). After 2 more days of suspension culture, $4 \times 10^6$ iPS cells collected by centrifugation (as above) were suspended in ES medium (0.1 to 10 ml), and seeded only in the indentations of the prepared pNIPAAm gel. This was cultured for a further 2 days to induce aggregation of the iPS cells, the gel was made to swell by lowering the ambient temperature to 25° C., and spherical three-dimensional cell aggregates were collected.

(3) Inducing Differentiation of Mouse iPS Cell Aggregates into Osteoblasts

The prepared iPS cell aggregates were seeded on a 60 mm tissue culture dish containing osteoblast differentiation-inducing medium (minimum essential medium Eagle, alpha modification (α-MEM medium: Nacalai Tesque) containing 10% fetal bovine serum (Invitrogen), 0.1 µM dexamethasone (Sigma), 10 mM β-glycerophosphoric acid (Sigma), 50 µg/ml ascorbic acid-2-phosphate (Sigma), 100 units/ml penicillin, 100 µg/ml streptomycin and 250 ng/ml amphotericin B (Invitrogen)) with a statin (1 µM simvastatin: Sigma) added thereto, and cultured for 20, 30, 40 and 50 days at 37° C., 5% $CO_2$ on a see-saw bioreactor (30° tilt, period 0.5 Hz, amplitude 12.5 mm) to prevent adherence to the dish, to induce the iPS cell aggregates to differentiate into osteoblasts. As a control, iPS cell aggregates were also cultured in osteoblast differentiation-inducing medium containing no statin.

(4) Tumor Formation by Mouse iPS Cell Aggregates 10 of the iPS cell aggregates that had been induced to differentiate into osteoblasts were mixed into a 20 mg/ml fibrinogen solution (Sigma) (0.05 to 1 ml), the same amount of a 12.5 U/ml thrombin solution (Sigma) was added, and gelling was induced by 30 minutes of still standing at 37° C. with 5% $CO_2$.

5-week-old male immunodeficient mice (C.B-17 SCID: CLEA Japan) were anesthetized by diethyl ether inhalation, and the prepared iPS cell aggregates contained in fibrin gel were transplanted under the dorsal skin. The mice were kept with free access to feed and water under specific pathogen-free conditions.

Figure 2:
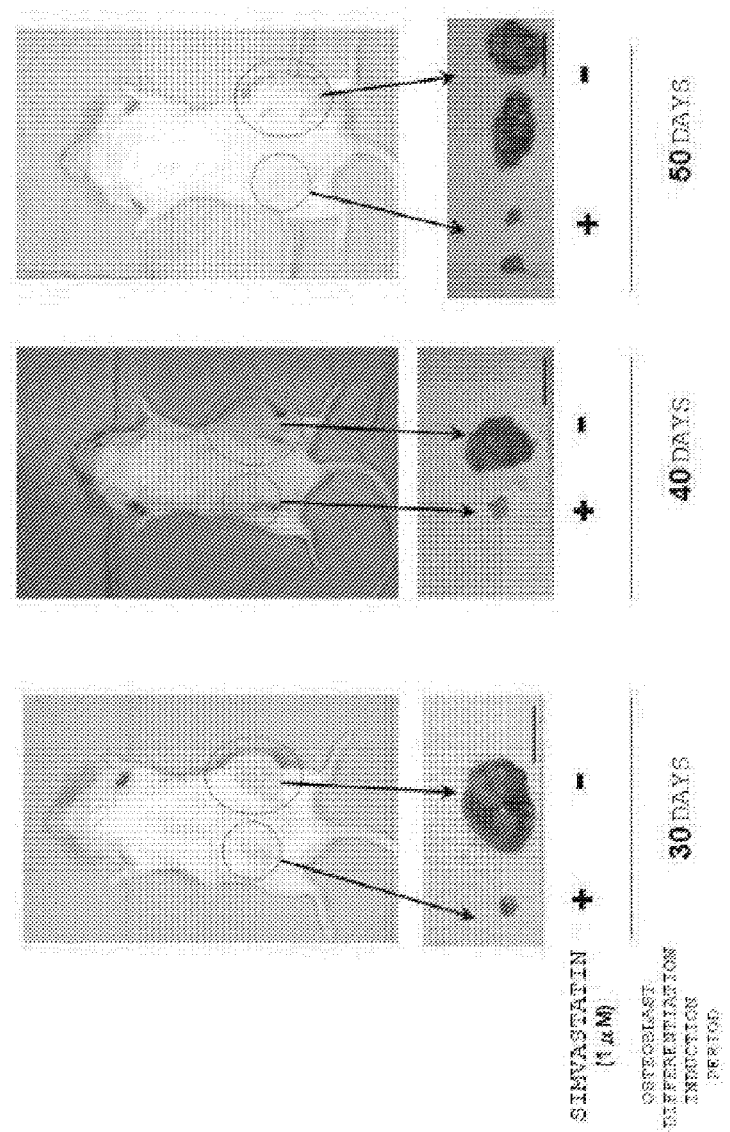
FIG. 2 shows the suppression effect of simvastatin on formation of tumors from iPS cells; When mice were kept for 28 days after transplantation of mouse iPS cells that had been subjected to 30 to 50 days of differentiation induction in osteoblast differentiation-inducing (+) medium containing simvastatin, no tumor formation by the grafts was observed; However, iPS cell grafts that had been subjected to differentiation induction in only osteoblast differentiation-inducing medium (−) exhibited obvious tumor formation (Bar: 1 cm).
Figure 3:
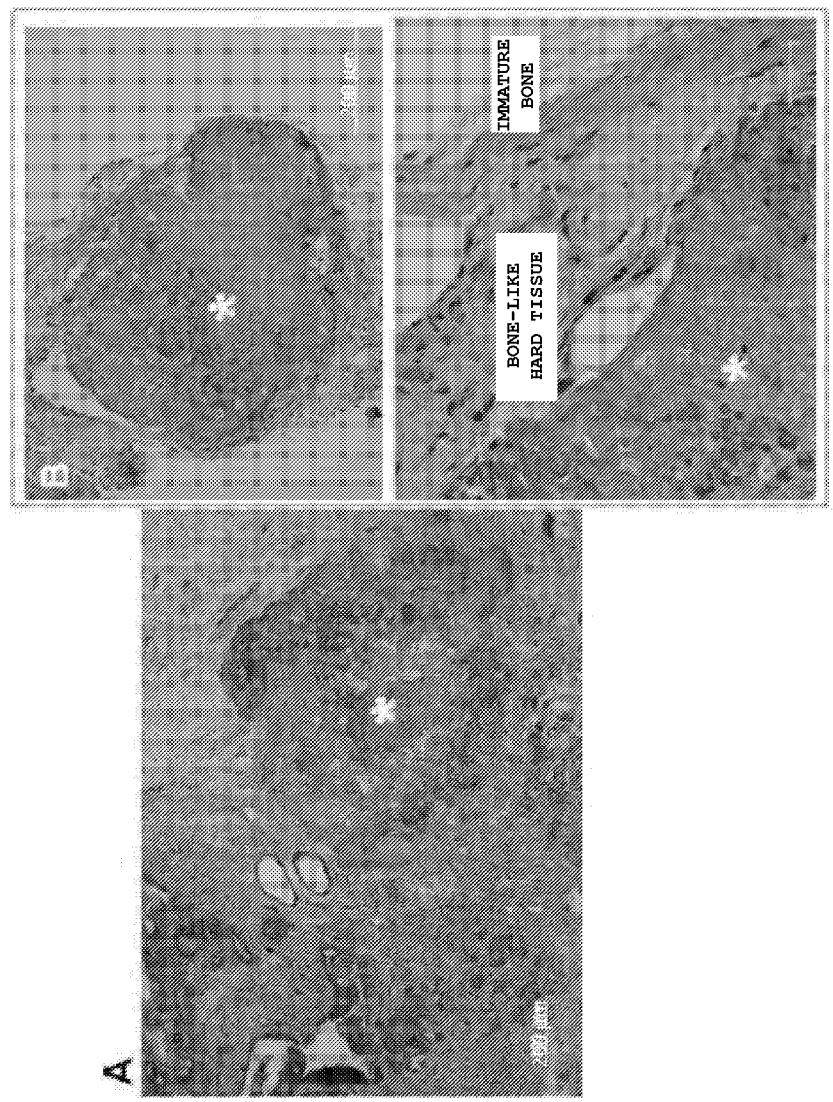
FIG. 3 shows that tumorigenesis after transplantation is suppressed by culturing iPS cells in the presence of simvastatin and an osteoblast inducing agent.
Figure 4:
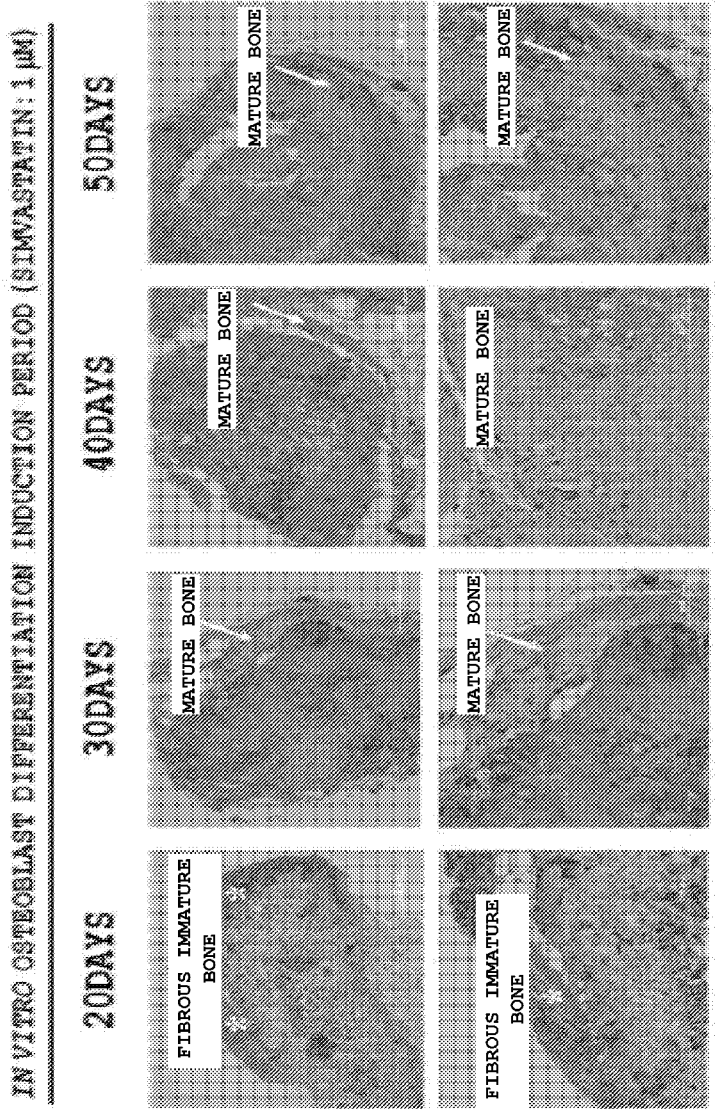
FIG. 4 shows photographs of H&E stains of grafts of mouse iPS cells that had been cultured for 20, 30, 40 and 50 days in osteoblast differentiation-inducing medium with added simvastatin, transplanted under mouse dorsal skin, and extracted 28 days after transplantation.
Figure 5:
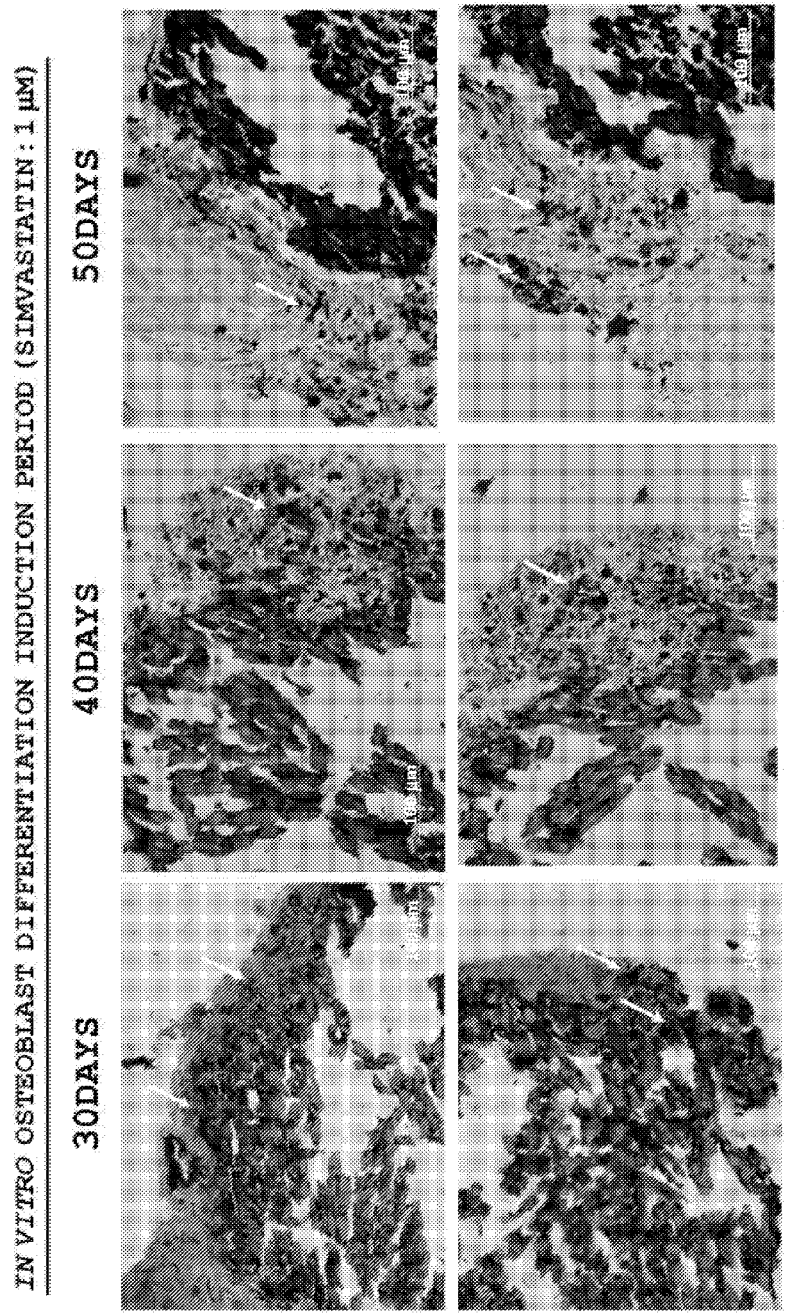
FIG. 5 shows photographs of methylene blue and Von Kossa stains of grafts of mouse iPS cells that had been cultured for 30, 40 and 50 days in osteoblast differentiation-inducing medium with added simvastatin, transplanted under mouse dorsal skin, and extracted 28 days after transplantation.
Figure 6:
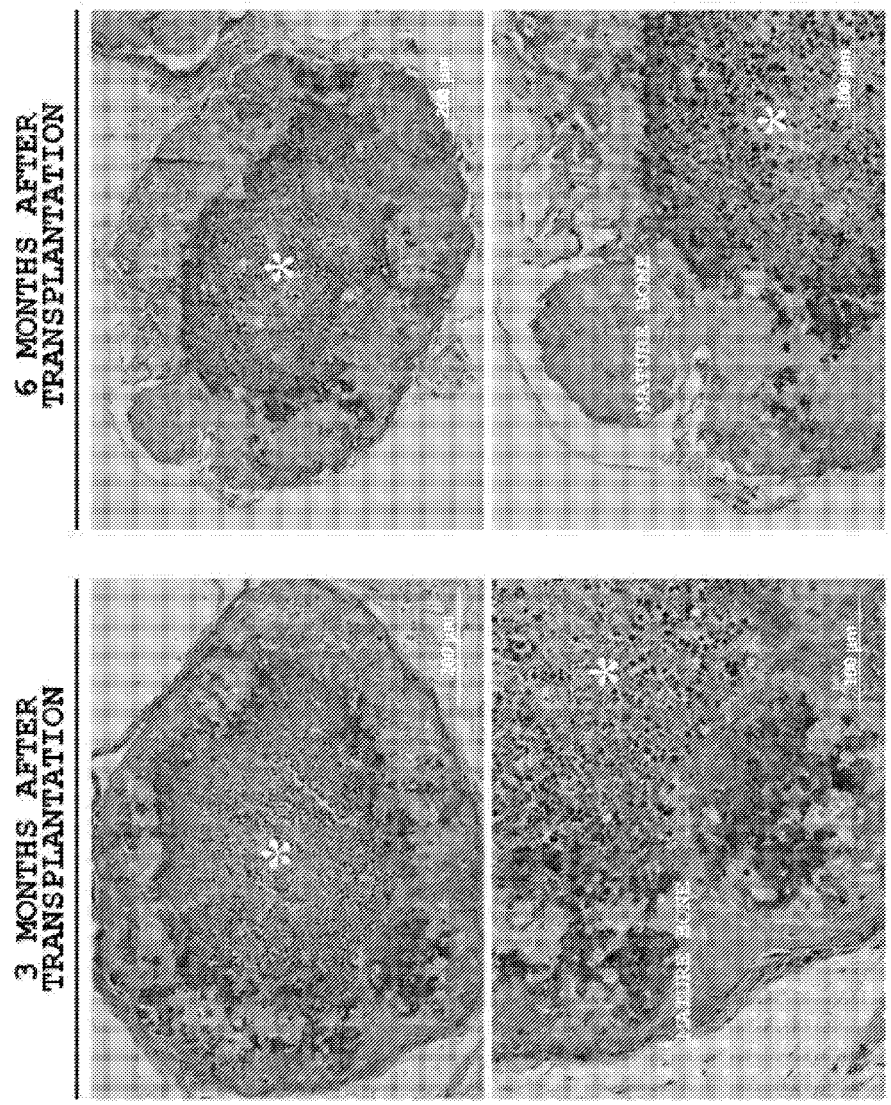
FIG. 6 shows photographs of H&E stains of grafts of iPS cells that had been cultured for 30 days in osteoblast differentiation-inducing medium with added simvastatin, transplanted under mouse dorsal skin, and extracted 3 months or 6 months after transplantation.

28 days after transplantation the transplanted grafts were extracted, and tumor formation was evaluated according to the size of the grafts. The results are shown in FIG. 1 and FIG. 2. The grafts were also immersion fixed with a 10% formalin neutral buffer solution, decalcified, and embedded in paraffin, and 3 µm-thick sections were prepared from the embedded samples. After hematoxylin and eosin (H&E) staining or methylene blue and Von Kossa staining on sample sections, the sections were observed histologically. The results of H&E staining are shown in FIG. 3 (differentiation induction period 30 days) and FIG. 4 (differentiation induction periods 20, 30, 40 and 50 days), while the results of methylene blue and Von Kossa staining are shown in FIG. 5 (differentiation induction periods 30, 40 and 50 days).

iPS cell aggregates were also subjected to 30 days of differentiation induction in the presence of simvastatin (1 µM) to obtain osteoblasts, which were transplanted under mouse dorsal skin. 3 months and 6 months after transplantation the extracted grafts were collected, and embedded in paraffin by the methods described above to prepare 3 µm-thick tissue sections. The resulting tissue sections were H&E stained, and subjected to histological observation. The results are shown in FIG. 6.

(5) Results

Formation of Tumors Caused by iPS Cell Transplantation

Using the methods described above under "(4) Tumor formation by mouse iPS cell aggregates", an iPS cell aggregate obtained in (2) above (that is, an iPS cell aggregate that had not undergone osteoblast differentiation induction) was transplanted into a mouse in place of cells obtained by inducing differentiation of iPS cells into osteoblasts, and observed histologically 28 days after transplantation to evaluate tumor formation. The cells that were transplanted without undergoing osteoblast differentiation induction had formed an obvious tumor around the graft 28 days after transplantation (FIG. 1A). Histological observation revealed that this tumor contained various ectodermal tissues (epidermal tissue, neural tissue), mesodermal tissues (cartilage tissue) and endodermal tissues (intestinal epithelial tissue) (FIG. 1B), indicating that this tumor was a teratoma derived from iPS cells that were undifferentiated at the time of transplantation.

Tumor formation was similarly observed (FIG. 1C) when iPS cells were induced to differentiate for 20, 30, 40 and 50 days in osteoblast differentiation-inducing medium containing no simvastatin in (3) above, and then transplanted.

When iPS cells were subjected to 50 days of osteoblast differentiation induction and then transplanted, formation of bone tissue was observed around the graft (FIG. 1D), and the tumor tended to be smaller (FIG. 1C). However, it was shown that tumor formation could not be avoided even when differentiation induction was performed for 50 days.

Suppression of iPS Cell-Derived Tumor Formation by Simvastatin

When mouse iPS cells were transplanted after being induced to differentiate for 30, 40 and 50 days in osteoblast differentiation-inducing medium containing simvastatin, and the mice were reared for 28 days, no tumor formation from the cell grafts was observed (+ in FIG. 2). On the other hand, the grafts of cells in which differentiation was induced with only osteoblast differentiation-inducing medium (no simvastatin contained) exhibited obvious tumor formation (− in FIG. 2).

The results of histological observation by H&E staining revealed various histologies typical of teratomas around the grafts of cells in which differentiation was induced with only osteoblast differentiation-inducing medium (around mark in FIG. 3A), while only formation of bone-like hard tissue and fibrous immature bone was observed around the grafts when differentiation was induced in osteoblast differentiation-inducing medium containing simvastatin (around mark in FIG. 3B). As shown in FIG. 4, moreover, formation of fibrous immature bone mark) was observed around the graft when the differentiation induction period was 20 days. When the differentiation induction period was 30, 40 and 50 days, formation of mature bone tissue was observed around the grafts. The presence of tissue other than bone tissue (tumorigenesis) was not observed, regardless of the differentiation induction period.

Histological observation by methylene blue & Von Kossa staining also revealed bone tissue exhibiting calcification (arrows) around the transplantation sites of cells obtained by inducing diversification of osteoblasts from iPS cells, regardless of whether the diversification induction period was 30 to 50 days (FIG. 5). The presence of tissue other than bone tissue (tumorigenesis) was not observed.

As shown in FIG. 6, moreover, formation of mature bone tissue was observed around the grafts (*) both 3 months and 6 months after transplantation when osteoblasts obtained by 30-day differentiation induction were transplanted. No tissue other than bone tissue (tumorigenesis) was observed in either case.

These results show that tumorigenesis after transplantation is clearly suppressed in osteoblasts obtained by inducing differentiation of iPS cell aggregates in the presence of simvastatin, in comparison with osteoblasts obtained by inducing differentiation without simvastatin.

Test Example 2

Tumorigenesis Suppression Effects of Statins iPS cell aggregates were prepared by the methods described in (1) and (2) of Test Example 1 above, and differentiation into osteoblasts was induced in osteoblast differentiation-inducing medium in the presence of statins. The differentiation induction conditions were those described in (3) of Test Example 1, using a lipophilic statin (simvastatin or fluvastatin) or hydrophilic statin (lovastatin) as the statin (1 μM each: Sigma). Statins are also known as compounds that promote osteoblast differentiation induction, and have the effect of differentiating iPS cells into osteoblasts. Osteoblasts obtained by inducing differentiation in the presence of an osteoblast differentiation induction promoter (phenamil 1 μM) that was not a statin (HMG-CoA reductase inhibitor) were used as a control.

Figure 7:
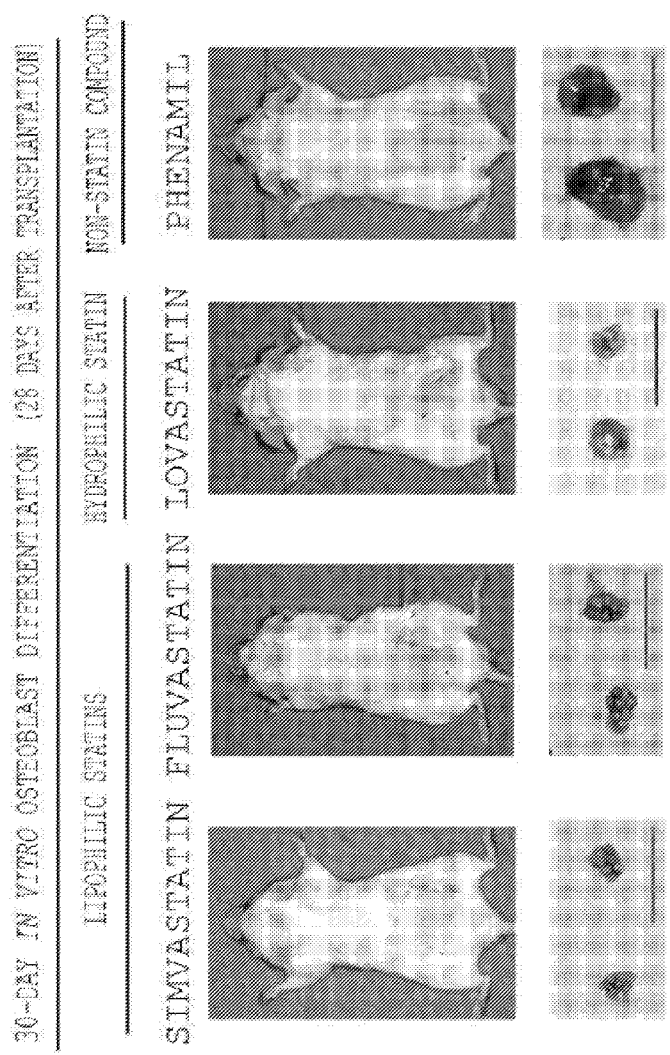
FIG. 7 shows photographs of mice 28 days after transplantation under the mouse dorsal skin of iPS cells that had been cultured for 30 days in osteoblast differentiation-inducing medium with a lipophilic statin, hydrophilic statin or phenamil added thereto, as well as photographs of the extracted grafts.
Figure 8:
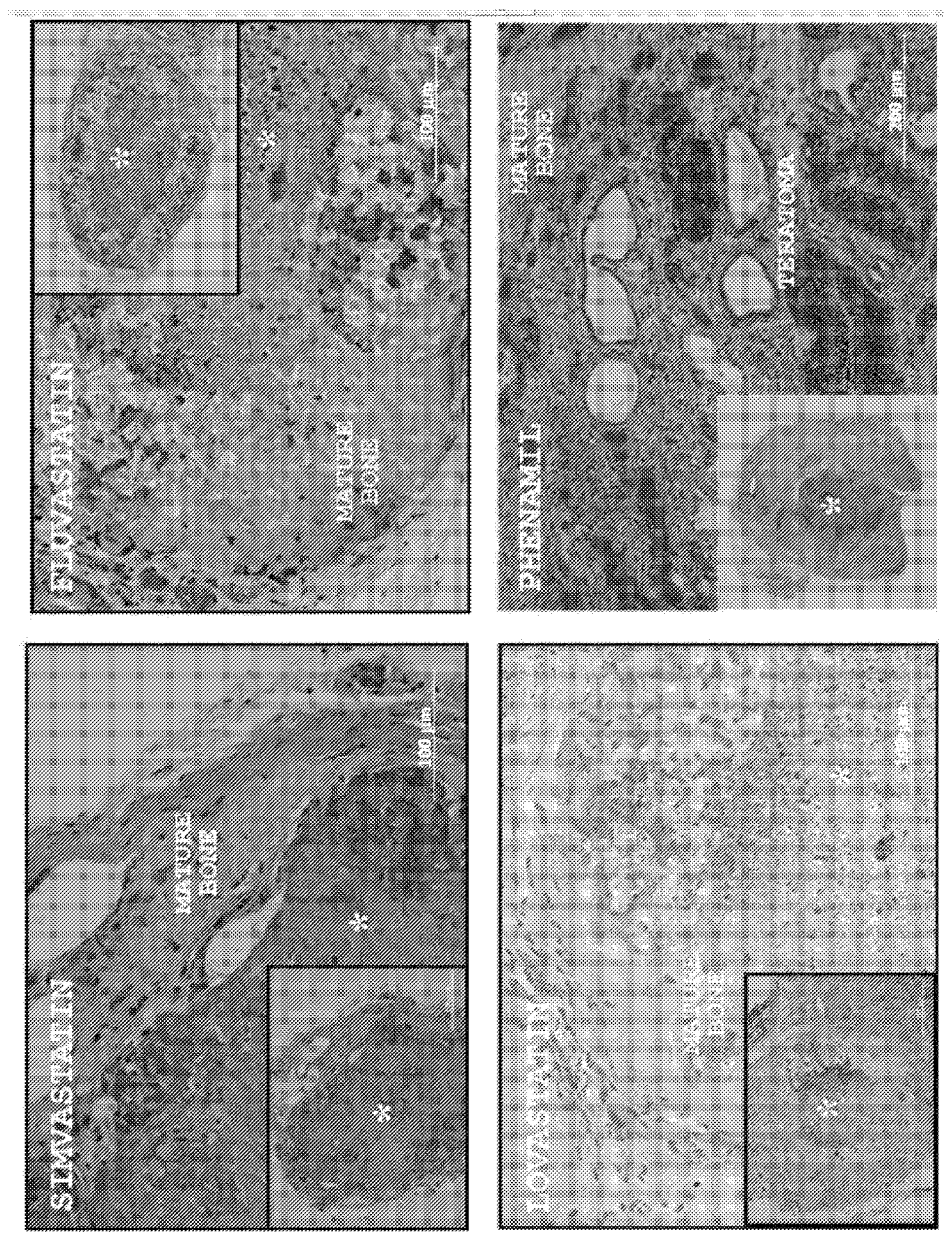
FIG. 8 shows photographs of H&E stains of grafts of iPS cells that had been cultured for 30 days in osteoblast differentiation-inducing medium with a lipophilic statin, hydrophilic statin or phenamil added thereto, transplanted under mouse dorsal skin, and extracted 28 days after transplantation.

Osteoblasts obtained by inducing differentiation for 30 days in the presence of a statin or phenamil were transplanted under mouse dorsal skin (both sides). The results are shown in FIG. 7. The upper part of FIG. 7 shows photographs of mice 28 days after transplantation, and the lower part shows photographs of the extracted grafts. FIG. 8 shows H&E stains of tissue sections of the grafts extracted after 28 days.

As shown in FIG. 7, lipophilic and hydrophilic statins exhibited tumor-suppressing effects, but a tumor was formed with the non-statin compound (phenamil). Moreover, as shown in FIG. 8, mature bone tissue was formed around the iPS cell grafts (*) with all the compounds. However, while no tissue other than bone tissue (tumorigenesis) was seen around the grafts in which differentiation had been introduced with lipophilic and hydrophilic statins, formation of tissue other than bone tissue (teratoma) was observed with the non-statin compound (phenamil).

As shown by the results of this test example, no tumor formation suppression effect was observed with other osteoblast differentiation induction promoting compounds such as phenamil. This shows even among the compounds that promote osteoblast differentiation induction, suppression of tumor formation is a characteristic effect of statins.

Test Example 3

Figure 9:
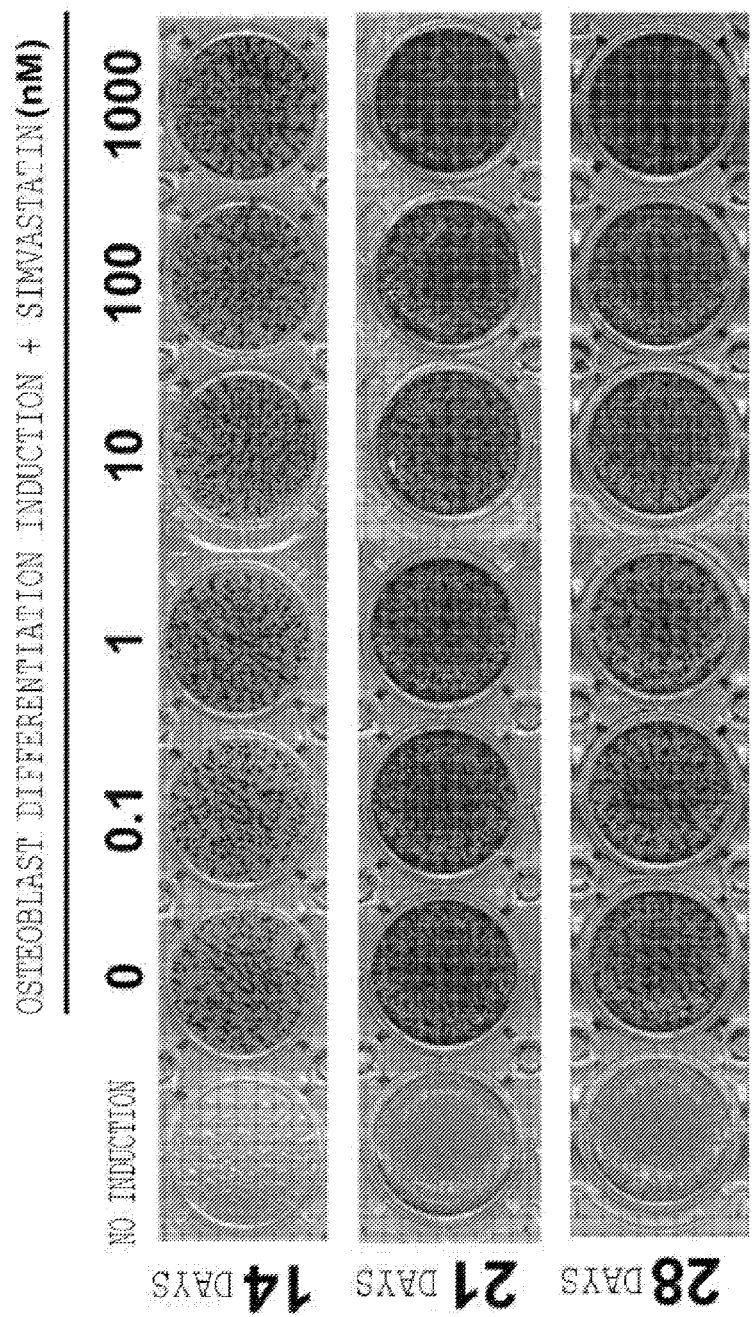
FIG. 9 shows photographs of azaline stains of iPS cells that had been induced to differentiate into osteoblasts in the presence of simvastatin (0 to 1000 nM).

Osteoblast Differentiation by Simvastatin, and Expression of Characteristic Genes for Osteoblast Differentiation Mouse iPS cells obtained by the methods described in (1) of Test Example 1 were induced to differentiate into osteoblasts for 14 to 28 days in the presence of simvastatin (0.1 to 1000 nM), using the osteoblast differentiation-inducing medium described in (3) of Test Example 1. After differentiation induction, calcification of the extracellular matrix was observed by alizarin staining. Alizarin staining was performed in accordance with the methods of Pagkalos et al. (Pagkalos J. et al., Journal of Bone and Mineral Research, Vol. 25, No. 11, pp 2470-2478). Calcified extracellular matrix is stained red by alizarin staining. FIG. 9 shows a photograph of stained cells. A simvastatin dose-dependent increase in the amount of red staining can be seen in FIG. 9, indicating promotion of diversification of mouse iPS cells into osteoblasts.

Mouse iPS cells obtained by the methods described in (1) of Test Example 1 were also induced to diversify into osteoblasts for 28 days in the presence of simvastatin (0.1 to 10 μM) using the osteoblast differentiation-inducing medium described in (3) of Test Example 1, and expression of genes specific to osteoblast differentiation (Osterix, Collagen I, Runx2, Osteocalcin) was analyzed by SYBR Green real time RT-PCR (Thunderbird® SYBR® qPCR Mix, Toyobo).

The nucleotide sequences of the primers used in SYBR Green real time RT-PCR were as follows.

```
Osterix forward primer:
                                    (SEQ ID NO: 1)
5'-CTCGTCTGACTGCCTGCCTAG-3'

Osterix reverse primer:
                                    (SEQ ID NO: 2)
5'-GCGTGGATGCCTGCCTTGTA-3'

Collagen I forward primer:
                                    (SEQ ID NO: 3)
5'-TGTCCCAACCCCCAAAGAC-3'

Collagen I reverse primer:
                                    (SEQ ID NO: 4)
5'-CCCTCGACTCCTACATCTTCTGA-3'

Runx2 forward primer:
                                    (SEQ ID NO: 5)
5'-CGGGCTACCTGCCATCAC-3'

Runx2 reverse primer:
                                    (SEQ ID NO: 6)
5'-GGCCAGAGGCAGAAGTCAGA-3'

Osteocalcin forward primer:
                                    (SEQ ID NO: 7)
5'-CCGGGAGCAGTGTGAGCTTA-3'

Osteocalcin reverse primer:
                                    (SEQ ID NO: 8)
5'-AGGCGGTCTTCAAGCCATACT-3'
```

GAPDH was also used as an internal standard. The nucleotide sequences of the primers for GAPDH were as follows.

```
GAPDH forward primer:
                                    (SEQ ID NO: 9)
5'-TGCACCACCAACTGCTTAG-3'

GAPDH reverse primer:
                                    (SEQ ID NO: 10)
5'-GGATGCAGGGATGATGTTC-3'
```

Figure 10:
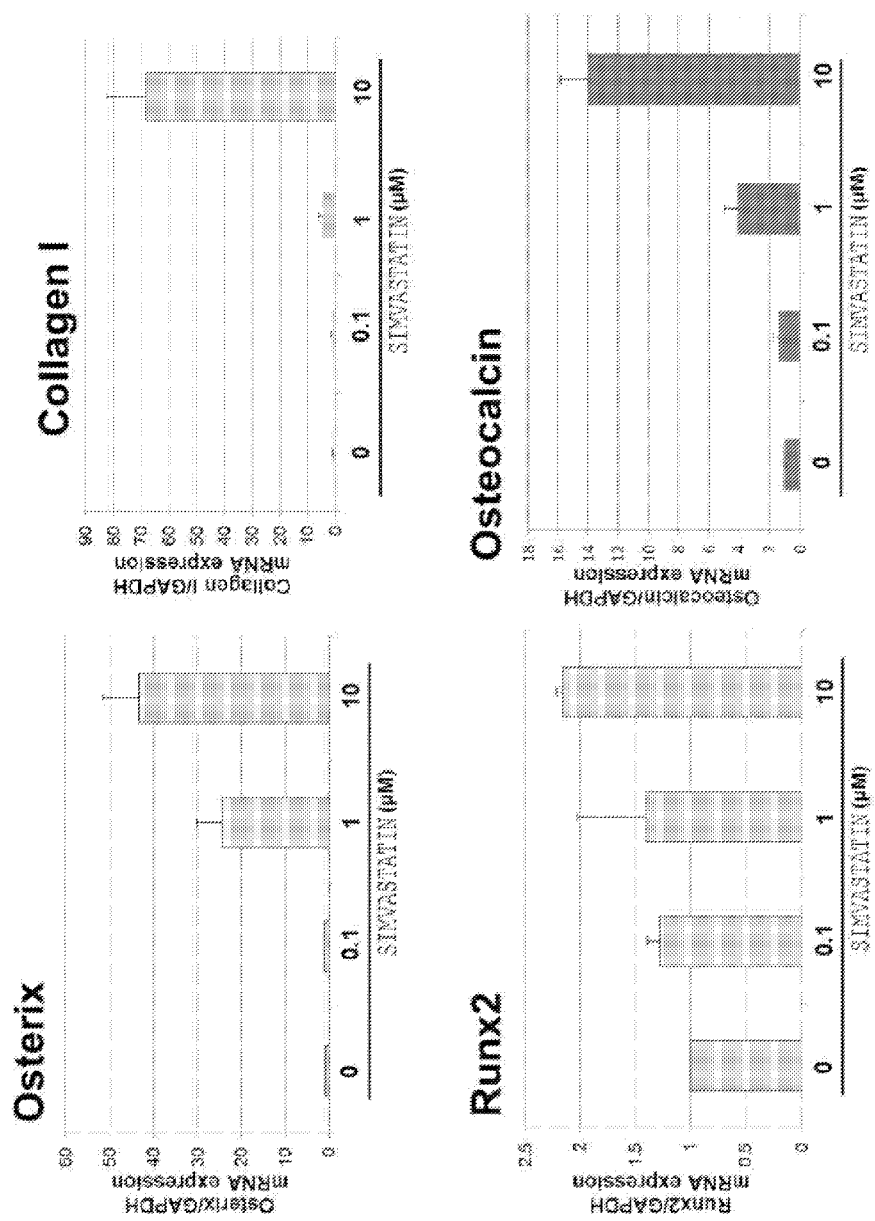
FIG. 10 is a graph showing the expressed amounts of osteoblast differentiation-specific genes in iPS cells that had been induced to differentiate into osteoblasts in the presence of simvastatin (0 to 10 μM).

The expressed amount of each gene is shown in the graph of FIG. 10. The expressed amounts of the mRNA of the osteoblast differentiation-specific genes are shown relative to the expressed amounts of GAPDH mRNA. FIG. 10 shows clearly that simvastatin dose-dependently promotes expression of these osteoblast differentiation-specific genes.

These results show that simvastatin dose-dependently promotes calcification of extracellular matrix and expression of osteoblast differentiation-specific genes in osteoblasts derived from iPS cells, and has an iPS cell osteoblast differentiation-promoting effect.

Test Example 4

Figure 11:
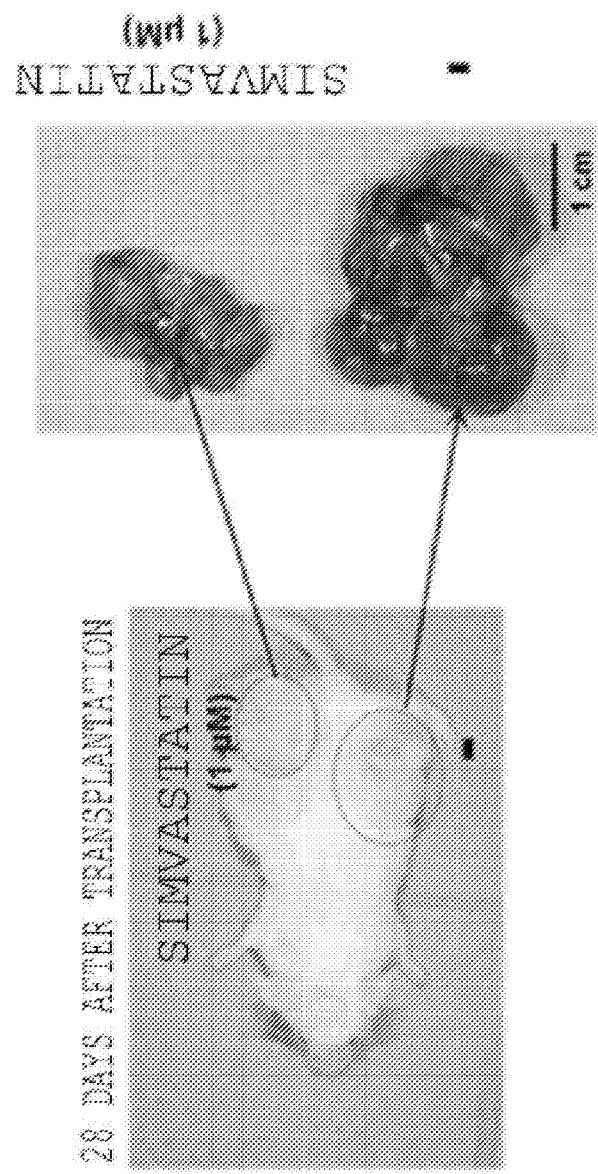
FIG. 11 shows a photograph of a mouse 28 days after transplantation under the mouse dorsal skin of iPS cell aggregates cultured in non-inducing medium either with or without simvastatin, together with a photograph of the extracted grafts.

Suppression of Tumor Formation in Non-Induced iPS Cell Aggregates by Simvastatin Suppression of Tumor Formation in Non-Induced iPS Cells In Vivo Mouse iPS cell aggregates obtained by the methods described in (1) and (2) of Test Example 1 were cultured for 20 days in non-inducing medium (ES medium, composition described in (1) of Test Example 1) with or without simvastatin (1 µM). These iPS cell aggregates were transplanted under mouse dorsal skin (left side: cultured without simvastatin, right side: cultured with simvastatin). FIG. 11 shows a photograph of the mouse 28 days after transplantation (left of figure), and photographs of the extracted grafts (right of figure).

As shown in FIG. 11, the iPS cells cultured with non-inducing medium formed tumors regardless of whether simvastatin was used, but tumor formation was less when the cells were cultured with simvastatin. This shows that simvastatin has a tumor-suppressing effect in iPS cells even in a non-differentiation-inducing system.

Cell Death of iPS Cells Due to Simvastatin

To investigate the effect of simvastatin on cell death in cultured iPS cells, mouse iPS cells obtained by the methods described in (1) of Test Example 1 were cultured for 10 days in non-inducing medium (ES medium) or osteoblast differentiation-inducing medium, with or without simvastatin (1 µM). The medium was exchanged every two days, at which time the number of cells in the culture supernatant was measured with a cell counter (Z1D: Beckman Coulter). The number of cells in each culture supernatant is shown on the vertical axis, and the number of days of culture on the horizontal axis (see FIG. 12).

Figure 12:
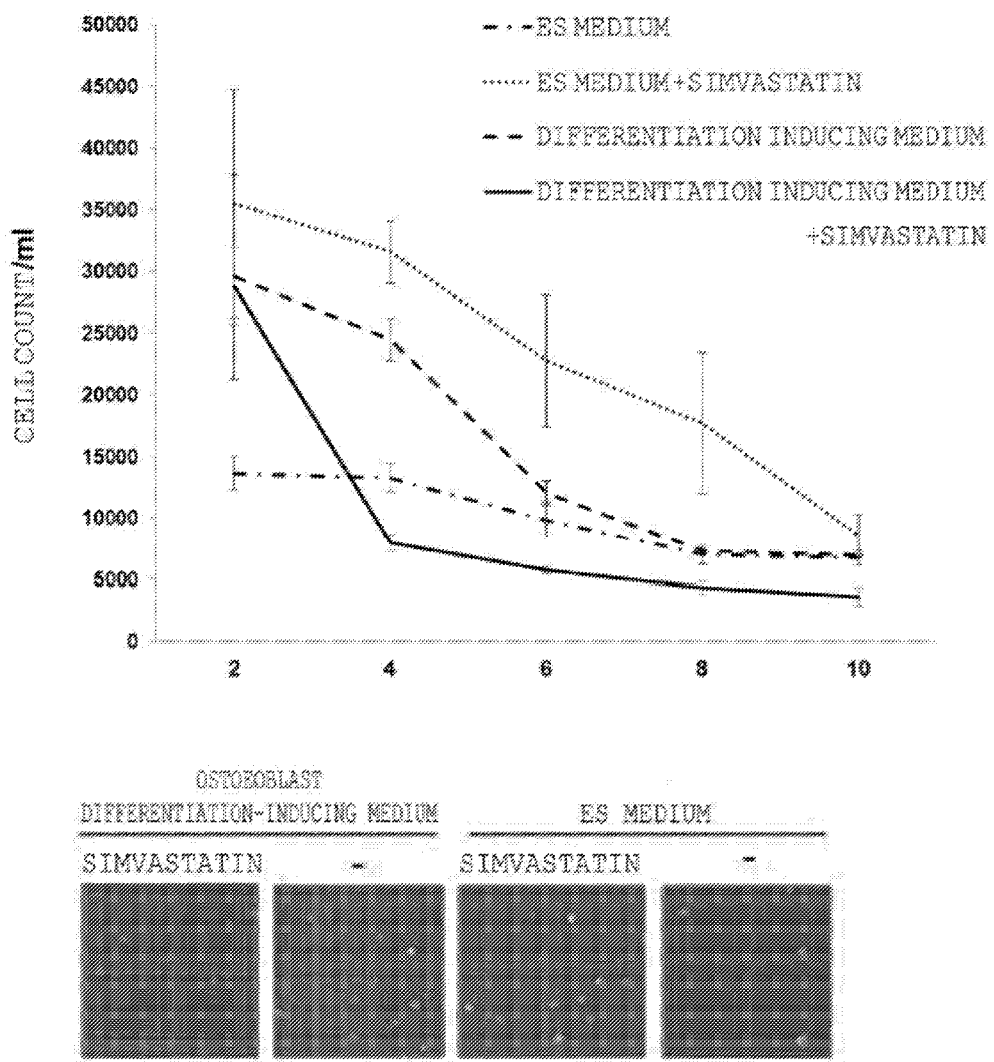
FIG. 12 is a graph showing floating cell numbers in culture supernatants of iPS cells cultured in non-inducing medium or osteoblast-inducing medium with or without simvastatin. The lower part shows photographs of cells of the cultured supernatants, stained with trypan blue.

As shown in the graph of FIG. 12, in non-inducing medium (ES medium) the iPS cells maintained their adherent state with relatively little separation. When cultured in osteoblast differentiation-inducing medium or in medium with added simvastatin, on the other hand, the adherent iPS cells tended to separate within 2 days and migrate into the culture supernatant. After 4 days, cell separation was less in the case of that iPS cells that were highly differentiated into osteoblast cells due to addition of simvastatin to osteoblast differentiation-inducing medium than it was under other conditions.

When the survival of cells in culture supernatant was investigated by trypan blue staining, death of 90% or more of the cells was confirmed under all conditions (FIG. 12, lower photographs), suggesting that separation of cells in culture supernatant was due to cell death. These results suggest that simvastatin may suppress tumors by causing cell death of undifferentiated iPS cells (that is, pluripotent stem cells with tumor-forming ability), while promoting osteoblast differentiation of the remaining iPS cells.

Inducing Apoptosis with Simvastatin in Undifferentiated iPS Cells

Figure 13:
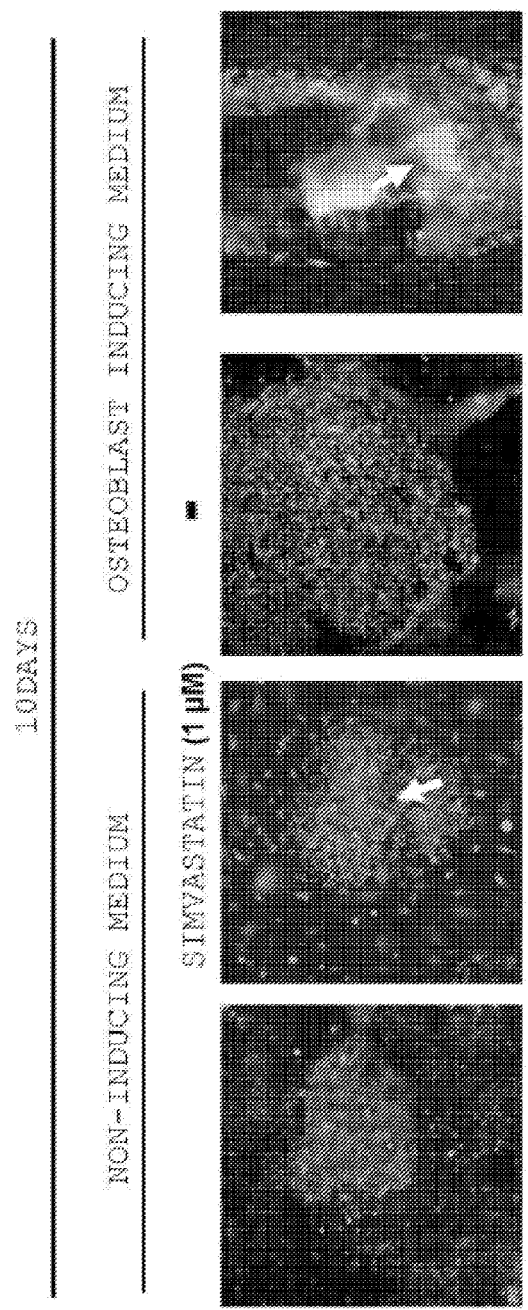
FIG. 13 shows photographs of the life or death of iPS cells cultured in non-inducing medium or osteoblast-inducing medium with or without simvastatin, as evaluated by a LIVE/DEAD Viability/Cytotoxicity Assay.

Mouse iPS cells were cultured for 10 days in non-inducing medium (ES medium) or osteoblast differentiation-inducing medium with or without simvastatin (1 µM), and cell survival was investigated by a LIVE/DEAD Viability/Cytotoxicity Assay (Invitrogen). The LIVE/DEAD Viability/Cytotoxicity Assay was performed in accordance with the report of Egusa et al. (Egusa H. et al., Tissue Eng. 2007; 13(10): 2589-2600), with live cells stained green and dead cells stained red. FIG. 13 shows photographs of stained cells.

As shown in FIG. 13, with simvastatin numerous dead cells (arrows) appeared in the centers of cell aggregates containing many undifferentiated iPS cells, regardless of whether differentiation was induced. This result suggests the possibility that simvastatin may suppress tumors by selectively inducing apoptosis of undifferentiated iPS cells having self-replicating ability (pluripotent stem cells with tumor-forming ability).

The results of Test Examples 1 to 4 above show that tumorigenesis is suppressed after transplantation in osteoblasts obtained by differentiating iPS cells in the presence of simvastatin and an osteoblast inducer. That is, it was shown that statins are effective at suppressing tumor formation by differentiated cells obtained from iPS cells. It was also shown that this tumor formation suppression effect is characteristic of statins among the known osteoblast inducers. Without trying to give a narrow interpretation of the present invention, moreover, it is believed that simvastatin suppresses tumors by selectively inducing apoptosis of undifferentiated iPS cells having self-replicating ability, while promoting osteoblast differentiation of the remaining iPS cells.

SEQUENCE TABLE FREE TEXT

SEQ ID NO:1 shows the Osterix forward primer.
SEQ ID NO:2 shows the Osterix reverse primer.
SEQ ID NO:3 shows the Collagen I forward primer.
SEQ ID NO:4 shows the Collagen I reverse primer.
SEQ ID NO:5 shows the Runx2 forward primer.
SEQ ID NO:6 shows the Runx2 reverse primer.
SEQ ID NO:7 shows the Osteocalcin forward primer.
SEQ ID NO:8 shows the Osteocalcin reverse primer.
SEQ ID NO:9 shows the GAPDH forward primer.
SEQ ID NO:10 shows the GAPDH reverse primer.

The invention claimed is:

1. A method for inducing differentiation of iPS cells while suppressing tumorigenesis, the method comprising:
adding to the iPS cells a statin and a differentiation inducer, wherein the differentiation inducer is known to cause differentiation of the iPS cells into osteoblasts, and
permitting differentiation of the iPS cells into osteoblasts, wherein the differentiation of the iPS cells is induced by the differentiation inducer, and wherein tumorigenesis is suppressed by the statin,
wherein the statin is a compound represented by General formula (A) below:

General Formula (a):

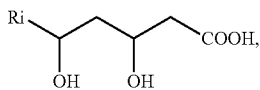

wherein the carboxyl group may form a ring structure with the hydroxyl group in the third position, and Ri represents any of the groups shown in General Formulas (1) and (2) below:

General Formula (1):

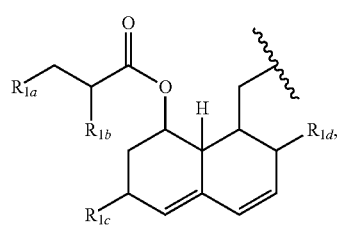

wherein $R_{1a}$ and $R_{1b}$ may be the same or different, and are each hydrogen atoms or $C_{1-5}$ linear or branched alkyl groups; and $R_{1c}$ and $R_{1d}$ may be the same or different, and are each hydrogen atoms, hydroxyl groups or $C_{1-5}$ linear or branched alkyl groups;

General Formula (2):

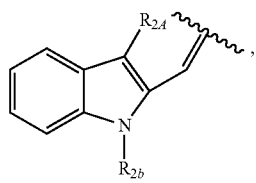

wherein $R_{2a}$ is a halogen-substituted phenyl group, and $R_{2b}$ is a $C_{1-5}$ linear or branched alkyl group.

2. The differentiation inducing method according to claim 1, wherein the statin is at least one selected from the group consisting of simvastatin, fluvastatin, lovastatin, and pravastatin.

3. The differentiation inducing method according to claim 1, wherein the iPS cells are differentiated into the osteoblasts by culturing the iPS cells in a medium containing the statin and the differentiation inducer.

4. The differentiation inducing method according to claim 1, wherein the iPS cells are differentiated into the osteoblasts by first culturing the iPS cells in a medium containing the statin, and then culturing the same in a medium containing the differentiation inducer.

5. The differentiation inducing method according to claim 1, wherein the concentration of the statin added to the iPS cells is 0.01 to 10 μM.

6. The differentiation inducing method according to claim 1, wherein the iPS cells are derived from epithelial cells or fibroblasts of an oral mucous membrane.

7. The differentiation inducing method according to claim 1, wherein the iPS cells are derived from epithelial cells or fibroblasts of an oral mucous membrane.

8. A method of preparing a cell preparation containing differentiated cells in which tumorigenesis is suppressed, the method comprising:
  adding to iPS cells a statin and a differentiation inducer, wherein the differentiation inducer is known to cause differentiation of the iPS cells into osteoblasts;
  permitting differentiation of the iPS cells into osteoblasts, wherein the differentiation of the iPS cells is induced by the differentiation inducer and wherein tumorigenesis is suppressed by the statin; and
  preparing a cell preparation that comprises the differentiated osteoblasts,
  wherein the statin is a compound represented by General Formula (A) below:

General Formula (a):

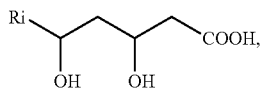

wherein the carboxyl group may form a ring structure with the hydroxyl group in the third position, and Ri represents any of the groups shown in General Formulas (1) and (2) below:

General Formula (1):

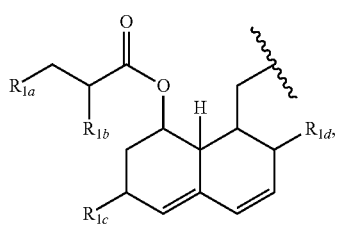

(1)

wherein $R_{1a}$ and $R_{1b}$ may be the same or different, and are each hydrogen atoms or $C_{1-5}$ linear or branched alkyl groups; and $R_{1c}$ and $R_{1d}$ may be the same or different, and are each hydrogen atoms, hydroxyl groups or $C_{1-5}$ linear or branched alkyl groups;

General Formula (2):

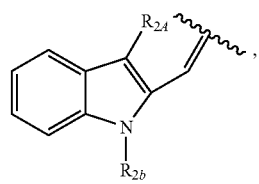

(2)

wherein $R_{2a}$ is a halogen-substituted phenyl group, and $R_{2b}$ is a $C_{1-5}$ linear or branched alkyl group.

9. A tissue regeneration method comprising:
  (i) adding a statin and a differentiation inducer to iPS cells, wherein the differentiation inducer causes differentiation of the iPS cells into osteoblasts;
  (ii) permitting differentiation of the iPS cells into osteoblasts, wherein the differentiation of the iPS cells is induced by the differentiation inducer, and wherein tumorigenesis is suppressed by the statin;
  (iii) preparing a cell preparation comprising the osteoblasts; and
  (iv) administering the cell preparation obtained in the step (iii) to a patient in need of regeneration of bone, wherein the bone in said patient is regenerated, and the statin is a compound represented by General Formula (A) below:

General Formula (a):

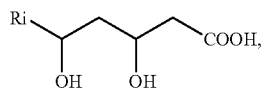

wherein the carboxyl group may form a ring structure with the hydroxyl group in the third position, and Ri represents any of the groups shown in General Formulas (1) and (2) below:

General Formula (1):

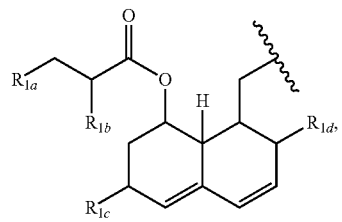

(1)

wherein $R_{1a}$ and $R_{1b}$ may be the same or different, and are each hydrogen atoms or $C_{1-5}$ linear or branched alkyl groups; and $R_{1c}$ and $R_{1d}$ may be the same or different, and are each hydrogen atoms, hydroxyl groups or $C_{1-5}$ linear or branched alkyl groups;

General Formula (2):

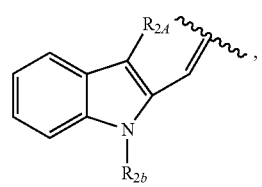

(2)

wherein $R_{2a}$ is a halogen-substituted phenyl group, and $R_{2b}$ is a $C_{1-5}$ linear or branched alkyl group.

* * * * *

SEQUENCE LISTING

```
<160> NUMBER OF SEQ ID NOS: 10

<210> SEQ ID NO 1
<211> LENGTH: 21
<212> TYPE: DNA
<213> ORGANISM: artificial sequence
<220> FEATURE:
<223> OTHER INFORMATION: Osterix forward primer

<400> SEQUENCE: 1
```

```
ctcgtctgac tgcctgccta g                                              21

<210> SEQ ID NO 2
<211> LENGTH: 20
<212> TYPE: DNA
<213> ORGANISM: artificial sequence
<220> FEATURE:
<223> OTHER INFORMATION: Osterix reverse primer

<400> SEQUENCE: 2
gcgtggatgc ctgccttgta                                                20

<210> SEQ ID NO 3
<211> LENGTH: 19
<212> TYPE: DNA
<213> ORGANISM: artificial sequence
<220> FEATURE:
<223> OTHER INFORMATION: Collagen I forward primer

<400> SEQUENCE: 3
tgtcccaacc cccaaagac                                                 19

<210> SEQ ID NO 4
<211> LENGTH: 23
<212> TYPE: DNA
<213> ORGANISM: artificial sequence
<220> FEATURE:
<223> OTHER INFORMATION: Collagen I reverse primer

<400> SEQUENCE: 4
ccctcgactc ctacatcttc tga                                            23

<210> SEQ ID NO 5
<211> LENGTH: 18
<212> TYPE: DNA
<213> ORGANISM: artificial sequence
<220> FEATURE:
<223> OTHER INFORMATION: Runx2 forward primer

<400> SEQUENCE: 5
cgggctacct gccatcac                                                  18

<210> SEQ ID NO 6
<211> LENGTH: 20
<212> TYPE: DNA
<213> ORGANISM: artificial sequence
<220> FEATURE:
<223> OTHER INFORMATION: Runx2 reverse primer

<400> SEQUENCE: 6
ggccagaggc agaagtcaga                                                20

<210> SEQ ID NO 7
<211> LENGTH: 20
<212> TYPE: DNA
<213> ORGANISM: artificial sequence
<220> FEATURE:
<223> OTHER INFORMATION: Osteocalcin forward primer

<400> SEQUENCE: 7
ccgggagcag tgtgagctta                                                20

<210> SEQ ID NO 8
<211> LENGTH: 21
<212> TYPE: DNA
```

```
<213> ORGANISM: artificial sequence
<220> FEATURE:
<223> OTHER INFORMATION: Osteocalcin reverse primer

<400> SEQUENCE: 8
aggcggtctt caagccatac t                                              21

<210> SEQ ID NO 9
<211> LENGTH: 19
<212> TYPE: DNA
<213> ORGANISM: artificial sequence
<220> FEATURE:
<223> OTHER INFORMATION: GAPDH forward primer

<400> SEQUENCE: 9
tgcaccacca actgcttag                                                 19

<210> SEQ ID NO 10
<211> LENGTH: 19
<212> TYPE: DNA
<213> ORGANISM: artificial sequence
<220> FEATURE:
<223> OTHER INFORMATION: GAPDH reverse primer

<400> SEQUENCE: 10
ggatgcaggg atgatgttc                                                 19
```